(12) United States Patent
Tolvanen et al.

(10) Patent No.: US 10,026,114 B2
(45) Date of Patent: Jul. 17, 2018

(54) SYSTEM FOR CLUSTERING AND AGGREGATING DATA FROM MULTIPLE SOURCES

(71) Applicant: BetterDoctor, Inc., San Francisco, CA (US)

(72) Inventors: Tapio Tolvanen, Cupertino, CA (US); Ari Tulla, San Francisco, CA (US); Tele Hao, Helsinki (FI)

(73) Assignee: BETTERDOCTOR, INC., San Francisco, CA (US)

( * ) Notice: Subject to any disclaimer, the term of this patent is extended or adjusted under 35 U.S.C. 154(b) by 296 days.

(21) Appl. No.: 14/594,933

(22) Filed: Jan. 12, 2015

(65) Prior Publication Data
US 2015/0199744 A1    Jul. 16, 2015

Related U.S. Application Data

(60) Provisional application No. 61/926,045, filed on Jan. 10, 2014.

(51) Int. Cl.
| | |
|---|---|
| *G06F 7/00* | (2006.01) |
| *G06Q 30/06* | (2012.01) |
| *G06F 17/30* | (2006.01) |
| *G16H 10/60* | (2018.01) |

(52) U.S. Cl.
CPC ..... *G06Q 30/0631* (2013.01); *G06F 17/3087* (2013.01); *G16H 10/60* (2018.01)

(58) Field of Classification Search
CPC .............. G06Q 30/0631; G06F 19/322; G06F 17/3087; G06F 9/3891; G06F 17/30598; G06F 19/707

USPC .......................... 707/737, 726, 748, 999.102
See application file for complete search history.

(56) References Cited

U.S. PATENT DOCUMENTS

| | | | | |
|---|---|---|---|---|
| 5,508,912 | A * | 4/1996 | Schneiderman | G06F 19/322 705/3 |
| 5,768,519 | A * | 6/1998 | Swift et al. | G06F 21/6218 707/999.009 |
| 8,370,328 | B2 * | 2/2013 | Woytowitz et al. | G06F 17/30731 707/719 |
| 8,533,223 | B2 * | 9/2013 | Houghton | G06F 17/241 707/759 |
| 8,843,501 | B2 * | 9/2014 | Allen et al. | G06Q 30/02 707/692 |

(Continued)

OTHER PUBLICATIONS

Empson, R., "With $2.6M From SoftTech, 500 Startups & More, BetterDoctor Wants to Take the Pain Out of Finding the Best Local Care", as downloaded on Mar. 19, 2014 from http://techcrunch.com/2013/10/22/with-2-6m-from-softtech-500-startups-more-betterdoctor-wants-to-take-the-pain-out-of-finding-the-best-local-care/, Oct. 22, 2013, 10 pages.

*Primary Examiner* — Mohammed R Uddin
(74) *Attorney, Agent, or Firm* — Kilpatrick Townsend & Stockton LLP

(57) ABSTRACT

Systems and methods are provided for receiving, aggregating, and analyzing data to develop caregiver rankings, recommendations, and other information that care seekers may use to connect with caregivers for services, or for caregivers to use to connect with care seekers. Sample data can be obtained from a plurality of data sources, processed to form data clusters, aggregated to form data records, and provided to a care seeker searching for a caregiver or medical facility.

25 Claims, 11 Drawing Sheets

(56) References Cited

U.S. PATENT DOCUMENTS

| | | | |
|---|---|---|---|
| 2004/0210763 A1* | 10/2004 | Jonas | G06F 17/30477 713/193 |
| 2006/0294092 A1* | 12/2006 | Giang et al. | G06F 17/30533 |
| 2007/0192122 A1* | 8/2007 | Routson et al. | G06Q 30/02 705/1.1 |
| 2008/0086387 A1* | 4/2008 | O'Rourke et al. | G06F 17/30867 705/26.1 |
| 2009/0089332 A1* | 4/2009 | Harger et al. | G06F 17/30303 |
| 2009/0089630 A1* | 4/2009 | Goldenberg et al. | G06F 17/30536 714/704 |
| 2009/0171955 A1* | 7/2009 | Merz et al. | G06F 17/30985 |
| 2009/0271348 A1* | 10/2009 | Allen et al. | G06Q 10/10 706/47 |
| 2010/0023515 A1* | 1/2010 | Marx | G06F 17/30598 707/E17.005 |
| 2010/0076972 A1* | 3/2010 | Baron et al. | G06F 17/3071 707/736 |
| 2010/0161566 A1* | 6/2010 | Adair et al. | G06F 17/30536 707/690 |
| 2010/0161634 A1* | 6/2010 | Caceres | G06F 17/30306 707/758 |
| 2010/0274815 A1* | 10/2010 | Vanasco | G06F 17/30867 707/798 |
| 2011/0055196 A1* | 3/2011 | Sundelin et al. | G06F 17/30539 707/711 |
| 2011/0317926 A1* | 12/2011 | Jonas | G06F 17/30303 382/209 |
| 2012/0185275 A1* | 7/2012 | Loghmani | G06F 19/328 705/3 |
| 2012/0197862 A1* | 8/2012 | Woytowitz et al. | G06F 17/30731 707/710 |
| 2013/0054598 A1* | 2/2013 | Caceres | G06F 17/30303 707/737 |
| 2013/0166552 A1* | 6/2013 | Rozenwald et al. | G06F 17/3071 707/737 |
| 2014/0066044 A1* | 3/2014 | Ramnani et al. | H04W 8/24 455/418 |
| 2014/0114949 A1* | 4/2014 | McClung et al. | G06F 17/30619 707/711 |
| 2014/0330845 A1* | 11/2014 | Feldschuh | G06F 17/30303 707/749 |
| 2014/0337331 A1* | 11/2014 | Hassanzadeh et al. | G06F 17/30578 707/726 |

* cited by examiner

FIG. 10

SYSTEM FOR CLUSTERING AND AGGREGATING DATA FROM MULTIPLE SOURCES

CROSS-REFERENCE TO RELATED APPLICATIONS

The present application claims priority from and is a non-provisional application of U.S. Provisional Application No. 61/926,045, entitled "CONNECTING CAREGIVERS TO CARESEEKERS," filed Jan. 10, 2014, the entire contents of which are herein incorporated by reference for all purposes.

FIELD

The present invention relates generally to clustering, aggregating, and filtering data to identify a caregiver for a care seeker.

BACKGROUND

Caregivers vary immensely in terms of their areas of specialty, experience, personality, and other measures. Given the diversity of the marketplace, it is all the more important for care seekers to be able to find the "right" caregiver for their health and wellness needs. Unfortunately, there are no tools currently available that adequately address this need.

When care seekers are unwell, finding the right caregiver can be physically and mentally exhausting. Even when healthy, this search can be frustrating because navigating the options requires time and focus. Care seekers have many things to consider, for example whether the caregiver is: in the care seeker's insurance network, is taking new patients and has openings available, is located within reach of the care seeker, is experienced in the areas of need, and has a personality that will correspond with that of the care seeker's.

Even if the care seeker knows all of the right questions to ask, access to some of the answers is often limited or totally restricted. Hours or days may be spent making phone calls and looking at web sites, yet care seekers may still not get the information they need to make an informed decision on selecting a caregiver. Existing tools have only limited utility. For instance, peer review websites offer limited, out-of-context information that may be only marginally helpful ("what does 3 stars actually mean with respect to a doctor?"). Further, caregiver referrals may be based on favoritism or other unseemly factors that do not coincide with care seeker interests.

Just as it is hard for a single care seeker to find information on caregivers, it is also difficult to compile information on many caregivers to assist care seekers with their search. First, data is scattered (for instance there is consumer data, provider data, insurance data, outcome data, government data, etc.), it may be hard to access, and its quality can be questionable. Data may be skewed (e.g. consumer reviews may slant negative), while provider reviews may generally be positive. Aggregation of the data is time consuming. Also, most data sources may not provide a standardized identifier associated with the caregiver (e.g., National Provider Identification (NPI) number, etc.). Because of these hurdles, it is difficult to compile objective rankings for caregivers. Further, the care seeker health information may not be easily accessible (e.g., information from insurance cards, doctor contact info, prescriptions are often out of reach, human error, unfamiliar words or numbers that are manually entered and/or incorrect, etc.), it is an even more difficult task to determine which caregivers are best for any given care seeker.

Caregivers may also have difficulty connecting with care seekers. For instance, booking patients and/or marketing their services may be a hassle for caregivers. As such, their marketing efforts may be outdated. Some marketing tactics may cause doctors caregivers to lose credibility (e.g., through a service that is known to be cheap or ineffective, etc.). It can be difficult to leverage current patients to grow business (e.g., unknown how to magnify word of mouth) and/or keep a constant flow of patients throughout the year (e.g., there are slow seasons, patients move, doctors find it difficult to use flexible pricing of procedures to attract clients when slow, etc.). Finally, caregiver office managers have high turnover, which further complicates the business of connecting with care seekers.

SUMMARY

The present disclosure relates to systems and methods for connecting caregivers with care seekers. Implementations may comprise a system or method of receiving, aggregating, and analyzing data to develop caregiver rankings, recommendations, and other information that care seekers may use to connect with caregivers for services, or for caregivers to use to connect with care seekers.

Other embodiments are directed to systems, portable consumer devices, and computer readable media associated with methods described herein.

A better understanding of the nature and advantages of embodiments of the present invention may be gained with reference to the following detailed description and the accompanying drawings.

BRIEF DESCRIPTION OF THE DRAWINGS

FIG. 10 shows a sample graphical user interface (GUI) according to an embodiment of the present invention.

DETAILED DESCRIPTION

The present disclosure describes systems and methods for connecting caregivers with care seekers. Embodiments of the disclosed system may employ data harvesting and/or intake, aggregation, and analysis to develop caregiver rankings, recommendations, and other information that care seekers may use to connect with caregivers for services, or for caregivers to use to connect with care seekers for business.

I. Method and System for Determining Caregivers for Care Seekers

Figure 1:
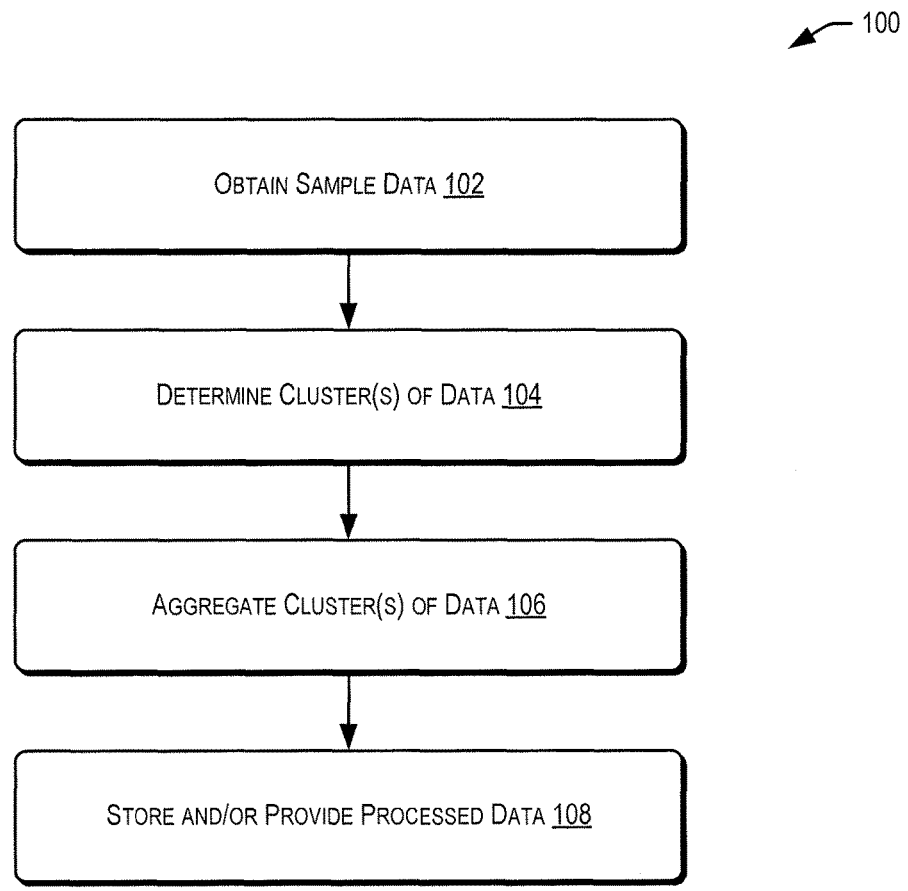
FIG. 1 shows a flowchart illustrating a method of clustering and aggregating data associated with a caregiver or medical facility according to an embodiment of the present invention.

FIG. 1 shows a flowchart illustrating a method of clustering and aggregating data associated with a caregiver or medical facility according to an embodiment of the present invention. The method 100 comprises one or more steps performed by a computer system, e.g., as illustrated in FIG. 2.

Figure 2:
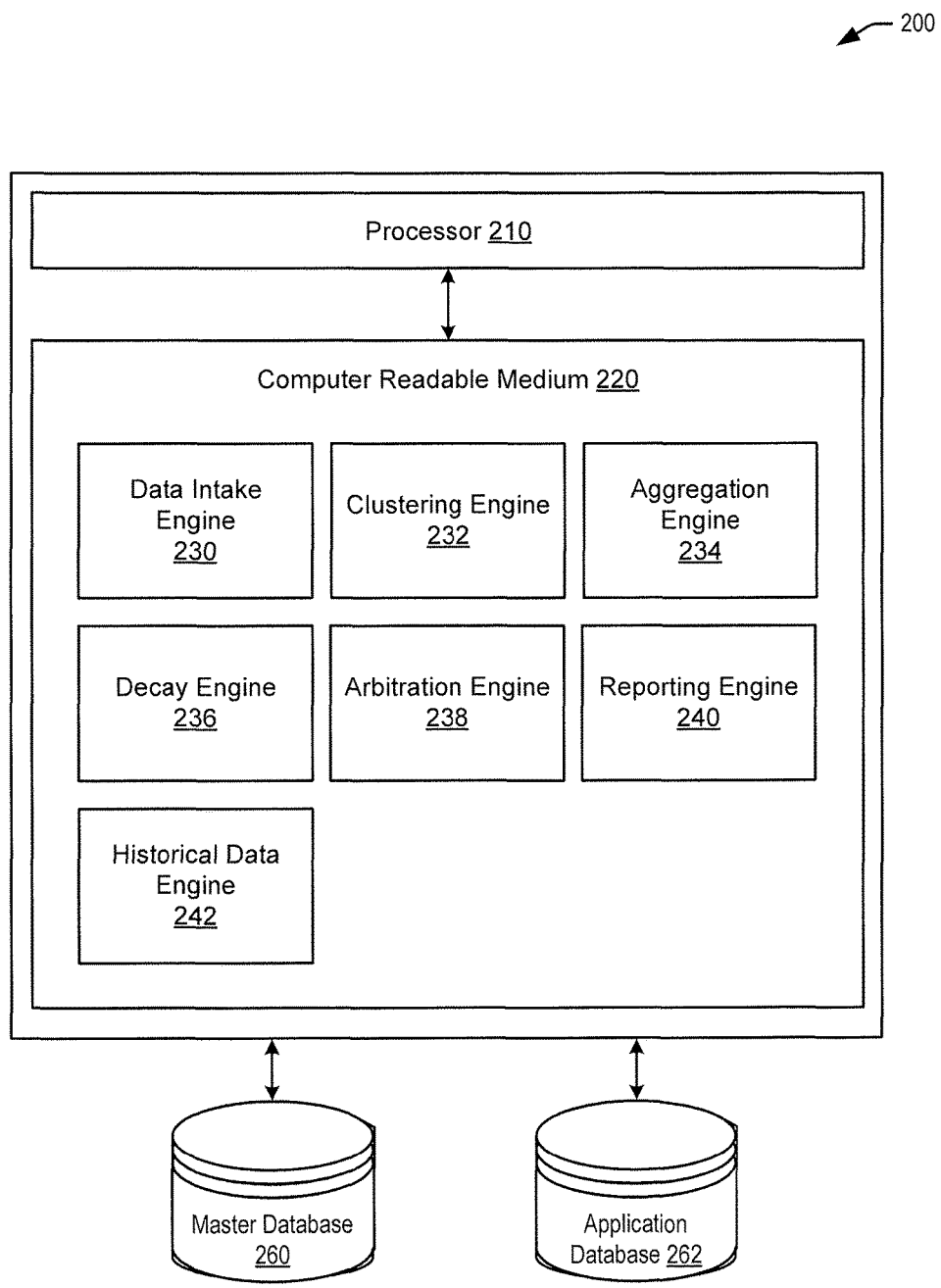
FIG. 2 shows an illustrative system for data sampling and acquisition according to an embodiment of the present invention.

FIG. 2 shows an illustrative system for data sampling and acquisition according to an embodiment of the present invention. The system 200 comprises at least a processor 210, computer readable medium 220, and one or more databases. The computer readable medium 220 can comprise one or more engines, including a data intake engine 230, clustering engine 232, aggregation engine 234, decay engine 236, arbitration engine 238, reporting engine 240, and historical data engine 242.

Returning to FIG. 1, at 102, sample data may be obtained. For example, the system 200 may obtain sample data from a plurality of data sources using the data intake engine 230. The data intake engine 230 may receive the sample data from one or more user devices (e.g., caregiver, care seeker, etc.), or other entities and devices providing government data, insurance data, billing records, and the like. Additional details regarding obtaining data and the corresponding data sources are provided with FIG. 3.

In some embodiments, the data from multiple data sources may correspond with the same entity. For example, the government data may include a data entry corresponding with Doctor Smith from San Francisco, the insurance data may include a data entry corresponding with Doctor Smith from San Francisco, and the care seeker feedback provided to a peer review webpage may include a data entry corresponding with Doctor Smith from San Francisco.

The sample data may be processed to identify a plurality of fields corresponding to each sample. For example, the sample data may include a plurality of text strings, symbols, and/or characters in a flat file (e.g., *.txt or *.csv, etc.). The data intake engine 230 may identify (e.g., parse, etc.) a name and geographical indicator associated with the plurality of fields in the data sample.

At 104, a plurality of clusters of data may be determined. For example, the system 200 may identify a first cluster of samples using the clustering engine 232. The first cluster may correspond with a first entity based on one or more rules. The cluster may help identify related data about a particular entity into a data object (e.g., Doctor Smith from San Francisco). In some embodiments, the clustering engine 232 implements several clustering algorithms and/or implements a clustering combination step after each clustering algorithm has been run. Additional clusters may be determined by determining whether a field distance between the two data samples is within a threshold. Additional details regarding clustering are provided with FIGS. 4-6.

At 106, the clusters of data may be aggregated to form data objects. For example, the system 200 may identify a first cluster and transform identified entity into a data object (e.g., Doctor Smith from San Francisco) using the aggregation engine 234. In some embodiments, data samples, clusters, and/or data fields may be removed from a corresponding entity using the decay engine 236. In some embodiments, a data source may be filtered, removed, supplemented, or otherwise altered based in part on analysis performed by the arbitration engine 238. In one or more of these engines of system 200, the data may be corrected and the most consistent and accurate data may be combined into a data object for display to a care seeker. Additional details regarding aggregation, decay, and arbitration are provided with FIGS. 7-8.

At 108, the processed data may be stored and/or provided. For example, the system 200 may provide the processed data to one or more caregivers or care seekers using the reporting engine 240. In another example, the system 200 may store the processed data in the master database 260 using the historical data engine 242. Information corresponding with the cluster may be stored in one or more databases (e.g., master database 260, application database 262, etc.). Additional details regarding storing and/or reporting data are provided with FIGS. 9-10.

II. Data Harvesting/Intake

Embodiments of the disclosure may receive and/or obtain data through data harvesting and/or data intake processes performed by the data intake engine 230.

A. Providing Data to the System from a Data Source

Figure 3:
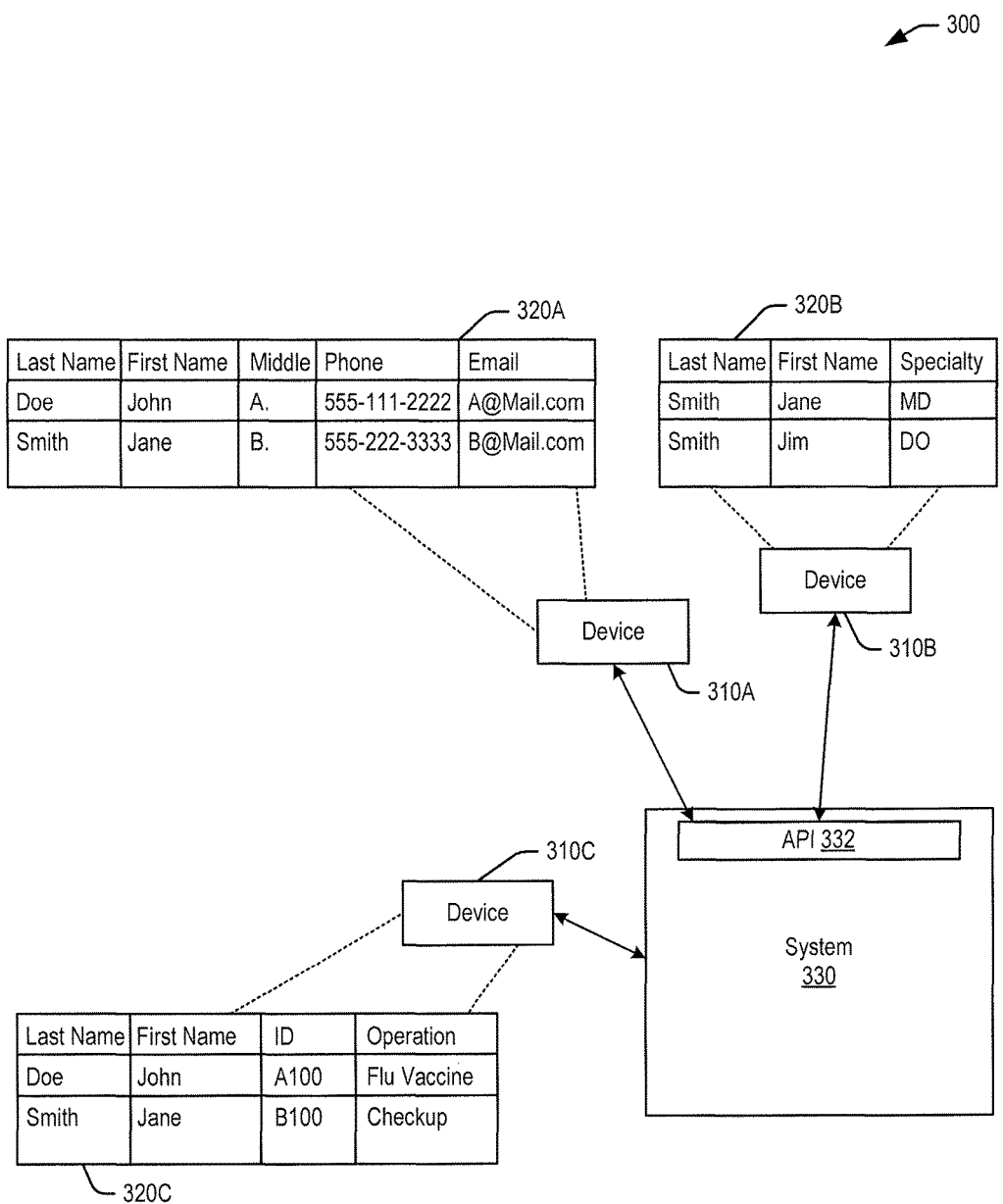
FIG. 3 shows an illustrative system for determining a caregiver for a care seeker according to an embodiment of the present invention.

FIG. 3 shows an illustrative system for determining a caregiver for a care seeker according to an embodiment of the present invention. In illustration 300, one or more data sources may include user device(s) 310A, 310B, 310C (hereinafter device 310) to provide data 320A, 320B, 320C (hereinafter data 320) to system 330. The system 330 may include an application programming interface (API) to accept the data. The data may also or alternatively be accepted directly from the device 310 through a different channel known in the art (e.g., via a file, data stream, or another method using data intake engine 230). An example of system 330 is illustrated in FIG. 2 as system 200.

In some embodiments, the data source (e.g., entity, device, etc.) may enroll with the system 330 to establish a profile or account. The data source may provide login credentials to access the account or passively provide credentials to access the account (e.g., providing an internet protocol (IP) address, storing a cookie or other data token on the device that is accessed by the system 330, etc.). In some examples, the data source may not provide login credentials and/or correspond with an account, but provide data anonymously.

The profile or account may correspond with a data format. For example, data source A may provide a caregiver's last name, first name, and phone number, in order, in a file, whereas data source B may provide a caregiver's first name, last name, and email address, in order. When the data source accesses the profile or account to provide the data, the received data may correspond with the known format associated with the profile.

The data source may provide data through various methods. For example, the device may transmit a file to system 330. The file may include a plurality of text strings, symbols, and/or characters in a flat file (e.g., *.txt, *.csv, *.xls, etc.). The data may correspond to a caregiver, care seeker, medical facility, etc. In some examples, the device may transmit data to system 330 through an application programming interface (API) in a particular format. When transmitted through the API, the system 330 may receive data that corresponds with pre-defined fields and/or a pre-defined format for receiving the data.

Data may include information about an entity (e.g., caregiver, medical facility, care seeker, etc.). For example, the data may include first name, last name, middle name or initial, gender, title (e.g., MD, PhD, doctor, assistant, etc.), address (e.g., work, secondary work address, home, etc.), phone number(s), website, geographic region, education, certifications, degrees, specialty, fellowship, school(s), residency, other qualifications, practice name, department, facility, description of the caregiver's practice (e.g., "Dr. Smith focuses on dental surgery . . . "), image, date of birth, languages spoken, availability to accept new patients, work hours/schedule, status, ratings or feedback, referrals, sanctions, malpractice, number of examination rooms available, insurance provider/plan, state insurance coverage, medical license number, unique identifier (e.g., National Provider Identification (NPI) number, database identifier, etc.), practice begin/end date, peer reviews, or other relevant information.

In some embodiments, the data is received or obtained by the system 330 (e.g., using the data intake engine 230). For example, the system 330 can extract the data from the data source using a method of ETL (extract transform load). The data source may provide the system 330 with access to the data and the system 330 may obtain the data from the data source.

In some embodiments, the data source may provide login credentials to access the account or passively provide credentials to access the account (e.g., providing an internet protocol (IP) address, storing a cookie or other data token on the device that is accessed by the system 330, etc.). In some examples, the data source may not provide login credentials or correspond with an account.

B. Data Sources

A plurality of example data sources are described below.

1. Data Provided by Caregivers/Care Seekers

Data may be received from caregivers, practice managers, users of system 330, and/or care seekers. For example, the system 330 can be configured to receive information from caregivers to update records of the caregivers and/or configured to receive information from care seekers to update records of the care seekers.

The caregiver or care seeker may be a data source. The caregiver may provide data through their account by using a device 310 (e.g., a personal computer, mobile or smart telephone, etc.) to access the system 330 and send data to it. For instance, a care seeker may specify their age, previous medical history, and other information, and send it to system 330. Caregivers, for example, may specify their practice's name, contact information, specialty, National Provider Identifier (NPI), and other information, and send it to system 330.

In some embodiments, the data source may be the caregiver providing feedback to the profile to update the data (e.g., associated with a higher confidence and/or priority than other data sources). The data source of the data may be changed to the caregiver in master database 260, and/or flagged to identify that the data has been updated by the caregiver. In some embodiments, an additional cluster may be generated and associated with the caregiver as the data source with a higher confidence value (described in Section III).

As illustrated, device 310A provides data 320A to system 330 through API 332. The data 320A includes information about a caregiver, including the caregiver's last name, first name, middle initial, phone number, and email address. The device 310A may include the caregiver's personal computer, smartphone, tablet, or other device operated by the caregiver or the caregiver's proxy.

2. Data Provided by Certification Data Sources or Public Sources

Data may be received from certification sources or public sources. For example, data may be received from government databases, provider identification data, and other data sources.

Data may be also be extracted from public sources (e.g., non-certification or government sources). For example, data published on a social networking website may be identified as a data source. The care seeker may provide their current location on the social networking website. The system may identify the data on the social networking website (or other third party data source) and obtain the data from the data source (e.g., through a web crawler, data extraction, saving a text string, etc.).

As illustrated, device 310B provides data 320B to system 330 through API 332. The data 320B includes information about a caregiver, including the caregiver's last name, first name and the certification and/or training associated with the caregiver (e.g., MD, DO, etc.). The device 310B may correspond with the certification data source or a data aggregator that accesses information from a plurality of certification data sources (e.g., universities, resumes, etc.).

3. Data Provided by Patient Records

Data may be identified from patient records. For example, the patient records can include past operations, prescriptions, diagnoses, or other information. The caregiver that identifies the particular diagnosis may be associated with the diagnosis. For example, the caregiver that identifies that a particular care seeker needs reading glasses may be associated with inspecting patients' vision later in the process. In some examples, a category of service (e.g., vision specialist, etc.) may be associated with the caregiver.

As illustrated, device 310C provides data 320C directly to the system 330 (e.g., using a flat file or the system receives the data through extraction/ETL). The data 320C includes information about a caregiver, including the caregiver's last name and first name, an identifier associated with the caregiver (e.g., National Provider Identification (NPI) number, etc.), and one or more operations performed by the caregiver on one or more patients (e.g., flu vaccine, annual checkup, etc.). The data may be obtained from invoices, patient records, data reporting services (e.g., Medical® or Medicaid® reporting services, etc.), or other data sources that can correlate caregivers' specialties or patient conditions treated with one or more caregivers.

4. Data Provided by Data Aggregators

Data may be received from data aggregators. For example, a data aggregator may aggregate data from a plurality government databases related to caregivers' practices. In some examples, the data aggregator may receive data from a plurality of peer review websites and certification data sources. In some examples, the data aggregator may include a web crawler or other search engine tool that gathers data from a plurality of sources to combine into a single data source. The system 330 may receive the aggregated data using the data intake engine 230 for further processing and analysis.

C. Formatting Data into Object Records

Data may be stored in one or more databases and/or data tables. In some embodiments, the data is provided to the system 330 are stored in a sample database and data that is formatted may be stored in a structured database as object records. In some embodiments, the data may be stored in a master database and correspond with flags or other identifiers to identify the corresponding type of data.

In some embodiments, the data is provided directly to the system 330 (e.g., not through the API) and may be formatted. The method of formatting data may correlate the data with object records, including a plurality of fields in one or more databases. For example, the object records may be stored in a proprietary data format. Raw data (sometimes herein referred to as "sample data") collected from the data sources can be identified and assigned a variable type. For example, sample data may be identified as a caregiver's name and is assigned a variable type specific to that category. The identification and assignment of data from its raw state to a proprietary data format (sometimes referred to as "structured data") may be processed using algorithms and/or with manual assistance.

In some embodiments, the data may be standardized. For example, an address may be compared with a data source that identifies a standard format for all addresses (e.g., United States Postal Service (USPS), etc.). The address from a secondary data source may be provided and/or updated to the standardized format provided by the USPS. In some embodiments, the system 330 (e.g., performed by the data intake engine 230) may include preprocessing where the data is cleaned, formalized, restructured, or associated to existing data formats. This allows better baseline for matching algorithms to operate (e.g., described in Section III) and/or find more matches of similar addresses that are meant to be associated with one another.

D. Enhancing Object Records Through Prioritization

In some embodiments, object records can be enhanced. For example, data sources may be prioritized so that when data from one data source conflicts with data from another data source, the data source associated with the higher prioritization may be used. In some embodiments, the database (e.g., master database 260) can include a priority field with one or more of the data entries. The system 200 can generate confidence levels and set priority rules to handle data depending on where it comes from, so that more trustworthy sources are relied upon than less trustworthy sources. This can enhance the overall accuracy of object records. In some embodiments, manual intervention may be used to resolve conflicts and otherwise enhance object records.

III. Clustering

Embodiments of the disclosure may cluster the data and/or object records performed by the clustering engine 232. For example, after raw data is transformed to structured data, the structured data can be clustered (e.g., algorithmically, through partial and optimized clustering, etc.). In some embodiments, the clustering engine 232 implements several clustering algorithms (e.g., forming their own set of clusters from the same sample data) and/or implement a clustering combination step after each clustering algorithm has been run.

A. Method of Clustering Data

Figure 4:
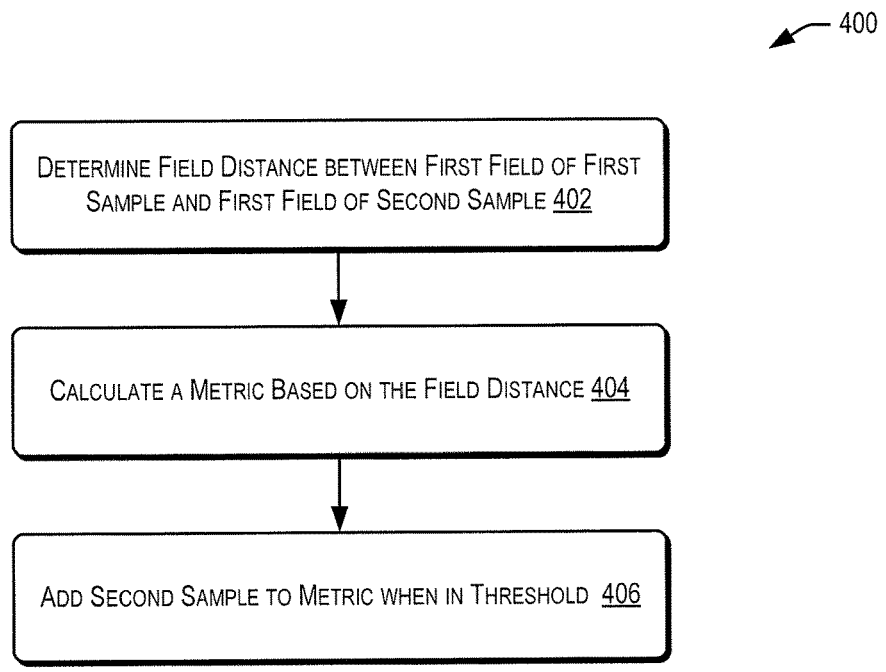
FIG. 4 shows a flowchart illustrating a method of clustering data according to an embodiment of the present invention.

FIG. 4 shows a flowchart illustrating a method of clustering data according to an embodiment of the present invention. The method 400 comprises one or more steps performed by a computer system, e.g., as illustrated in FIG. 2. In some embodiments, the method 400 may correspond with 104 in FIG. 1 to describe one or more steps associated with determining a cluster of data. Additional details regarding clustering are provided throughout this Section III.

A first cluster corresponding to a first entity may be identified, based on one or more rules. For example, the first cluster of the samples may correspond to a first entity based on a first set of rules. The first cluster can include a first sample.

The first cluster may be identified using a variety of methods. For example, the system 200 may determine whether a second sample is in the first cluster in order to identify a first cluster. The second sample may be included with the first cluster based in part on a field distance, metric, and a comparison with a threshold. In some examples, the clustering may involve two steps, where a plurality of different sets of clusters are first clustered by different fields, and then combined as optimized clusters.

At 402, the field distance may be determined between a first field of the first sample and the first field of the second sample. For example, the field distance may identify the relative similarity between two data fields, entities, or other data types. The field distance may include a calculated representation of the difference between two data samples (e.g., through fuzzy logic, algorithmic processing, string matching, fuzzy feature contrast (FCC), local sequence comparison, etc.).

At 404, the first metric may be calculated based on the first field distance. The metric(s) can be any unit of measurement to compare two fields, including the field distances, text string lengths, confidence values, priority associated with the data source, and others discussed throughout the disclosure.

At 406, the second sample may be added to the first metric when the first metric is within a first threshold. This may include when the metric is within a threshold, including more than 75% matching, less than 10% different, or other examples explained herein.

B. Clustering Illustration

Figure 5:
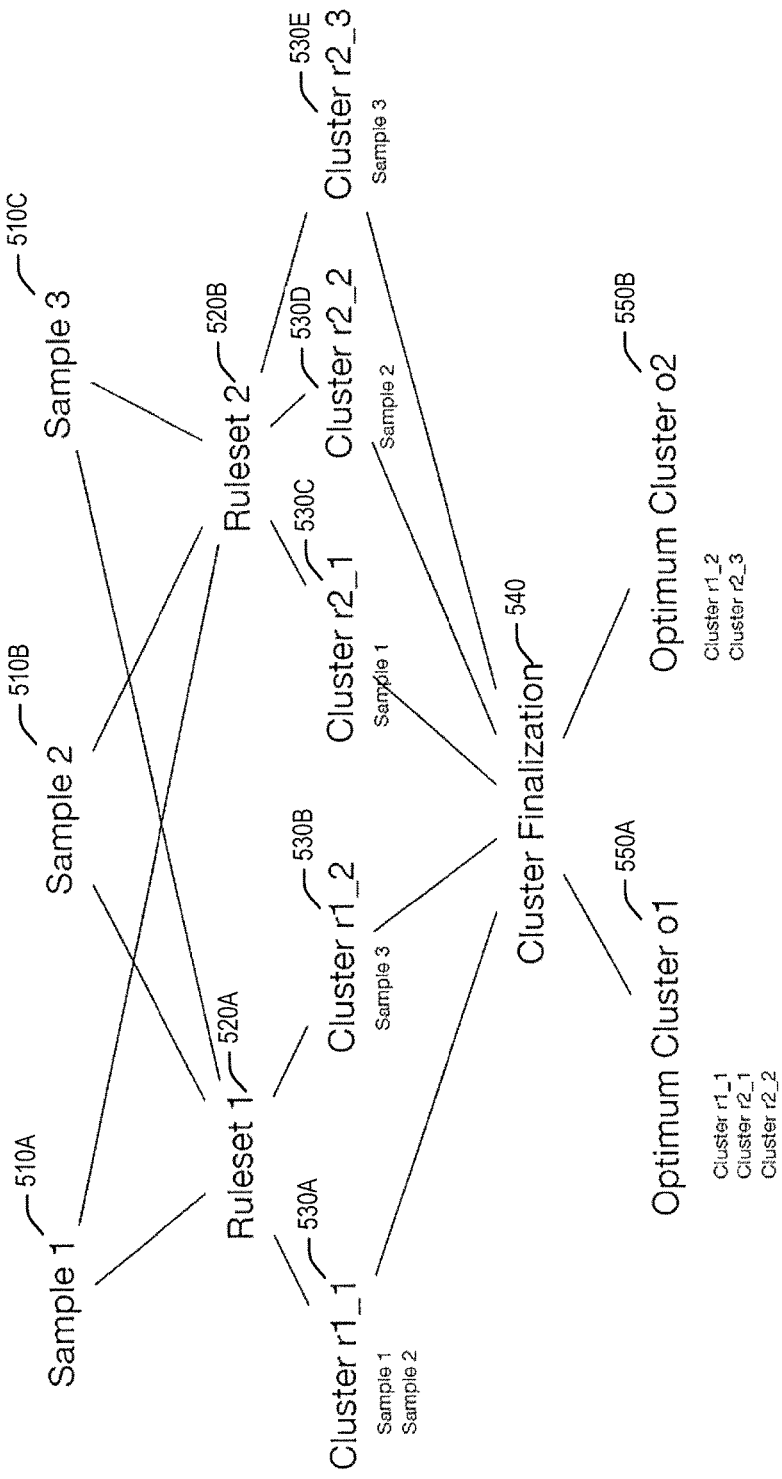
FIG. 5 shows an illustrative example of clustering data according to an embodiment of the present invention.

FIG. 5 shows an illustrative example of clustering data according to an embodiment of the present invention. In illustration 500, the clustering illustration may begin with a plurality of data sources that provide sample data 510A, 510B, and 510C (hereinafter "sample data 510"). The sample data may include structured or unstructured data, which may be standardized into a particular format.

The data samples may be processed by one or more rule sets or algorithms 520A and 520B (hereinafter "algorithms 520"). Each of these algorithms may implement one or more clustering algorithms. In some embodiments, the resulting clusters 530A-530E can be used in an aggregation process. In other embodiments, clusters 530A-530E can be clustered, as is shown in FIG. 5.

The algorithms 520 may contain different sample data fields/attributes to relate entities together from different perspectives. One perspective can be name matching, other can be unique identifier matching, etc. Additional details are provided in Section III Subsection E.

C. Database Associated with Clustering Entity Data

Figure 6:
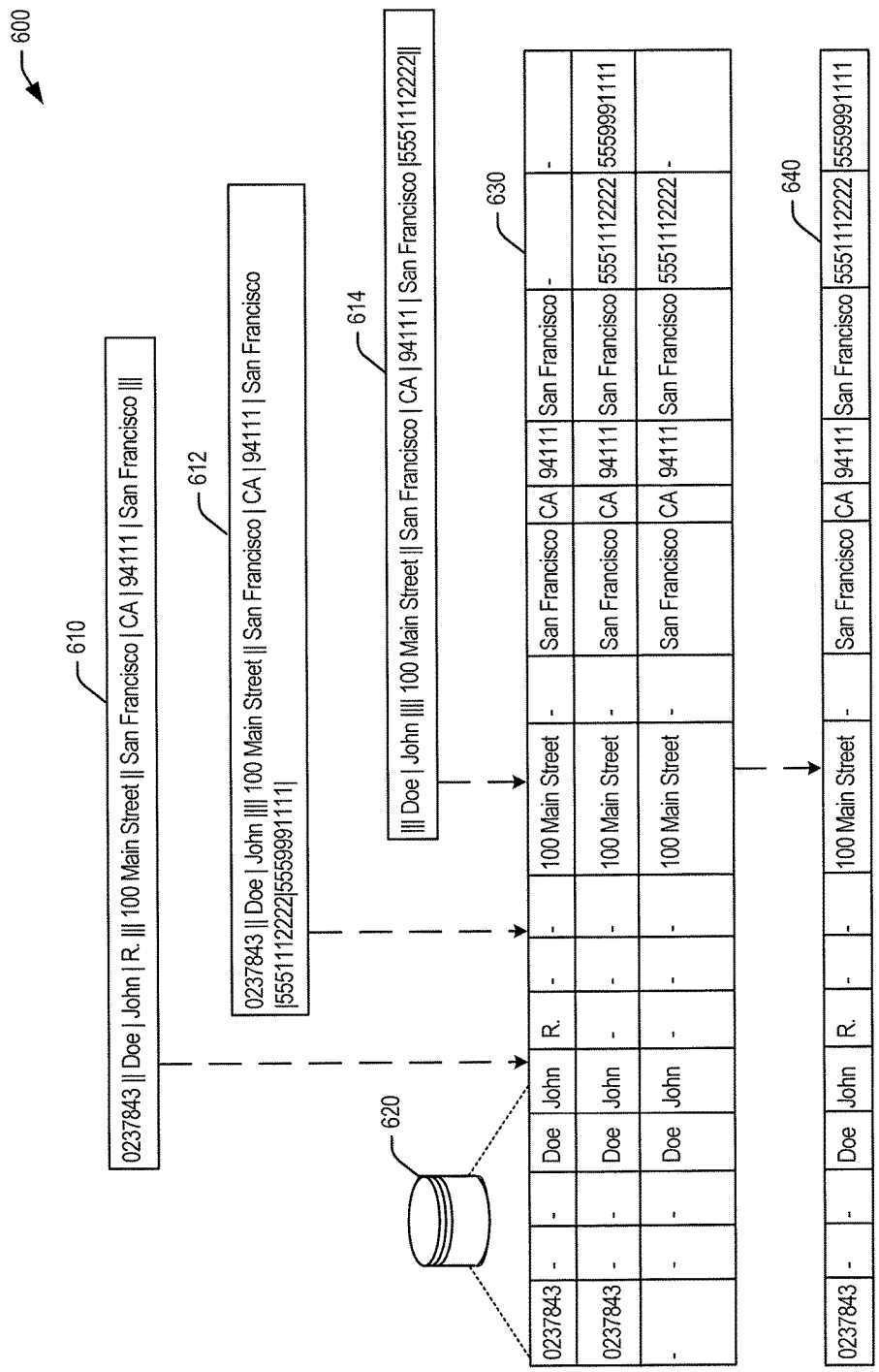
FIG. 6 shows an illustrative database associated with clustering data according to an embodiment of the present invention.

FIG. 6 shows an illustrative database associated with clustering data according to an embodiment of the present invention. In illustration 600, structured data 610, 612, 614 is received at database 620 (e.g., via system 330) and is clustered to create data cluster 630. The clustered data 630 is then aggregated to form an optimized cluster 640 during aggregation (described in Section IV). The structured data may be received from a plurality of data sources through an API, as illustrated in FIG. 3. The structured data may be processed to correspond with a plurality of fields in the database, and added to database 620 as clustered data 630 (e.g., one field for a last name, one field for a first name, one field for an identifier, etc.). Each cluster may correspond with a single entity (e.g., caregiver, care seeker, facility, etc.) and one or more clusters may be generated. As illustrated in 600, cluster 630 may represent the optimum cluster and/or include similar entries that may be associated with one another, identified through the clustering process.

D. Algorithms for Clustering

New object records may be created through algorithmic clustering of sample data based on different properties of the sample data, such as address, name, or identifiers (e.g., NPI). Algorithmic clustering may be used to identify the field distance of two text strings, clusters, data sets, or other information. The clustering may implement a plurality of algorithms and one or more of the algorithms. In some examples, the algorithms may include unique identifier-based matching, address matching (e.g., street, city, state, zip, country, etc.), string matching (e.g., caregiver's first name, last name, practice name, etc.), combined phone number and location matching, combined name and phone number matching, combined name and medical school and graduation year matching, combined name and specialty matching, geographical distance-based matching, standardization of one or more data fields or text strings to accelerate the matching, phonetic algorithms, or other types of matching. In some examples, the algorithms are combined (e.g., address and phone matching, etc.) and/or prioritized (e.g., less expensive to implement, faster or better results, etc.).

Unique identifier-based matching may compare a first and second identifier provided by different data sources (e.g., identifier assigned to a previously-generated cluster for a series of data fields, identifier determined by a certification data source, NPI, etc.). Each character from the first identifier may be sequentially compared with each character from the second identifier. In some embodiments, the comparison is expedited by comparing an identifier length or other aspects of the identifier (e.g., a portion of the identifier, only the characters in the identifier, etc.) in order to determine the distance between the two identifiers.

As an illustration of unique identifier-based matching, the first identifier is A123456 and the second identifier is B123459. The identifiers may be compared, character by character, so that A is compared with B, 1 is compared with 1, 2 is compared with 2, and so on. The number of differences between the two identifiers may be added to create the field distance. In this illustration, the field distance between A123456 and B123459 would be two (e.g., A and B are different, and 6 and 9 are different, resulting in two differences). Other implementations of unique identifier-based matching may be used as well, including a percentage similarity (e.g., out of seven characters, five characters match, causing an approximately 71% similarity or 71 out of 100 distance, etc.) or a relative difference out of a scale (e.g., 0.7 out of 1.0, etc.). With other implementations, the field distances may identify these differences as well (e.g., 71% similar, etc.). The field distance calculation and/or algorithms may be determined based in part on one or more of these representative fields in each cluster (e.g., name, address, identifier, etc.).

In some embodiments, the fields are compared non-sequentially. For example, the algorithm may identify the longest common sequence (LCS) of the two identifiers. In the illustration, the sequence may include "12345" in the middle of the text string, not accounting for the first character or last digit.

Address matching may compare a first and second address from different data sources to determine a field distance for the address field. For example, a street number, street name, suite/apartment, city, state, and zip code from one data source may be compared with the same data fields from a second data source (e.g., character by character, as a complete or standardized text string without spaces, etc.). In some embodiments, the field distance for the individual fields that combine to create an address may be associated with separate field distances, and aggregated to determine a total field distance (e.g., street number is compared with street number, street name is compared with street name, etc.). Some fields may be weighted (e.g., city may be more important than street name resulting in a higher weight for city over street name, etc.) or concatenated (e.g., zip code may be limited to 5 digits instead of 9 digits when determining field distance, etc.).

In some embodiments, address matching may perform a two-step process. For example, the first and second address may be compared by zip code as the first step (e.g., standardized zip codes, a portion of the zip code, etc.). When the zip codes do not match, the address matching may stop and/or identify a non-match or a poor field distance. The address may be filtered or removed from the analysis. If the zip codes do match, the remainder of the address may be matched through address matching or another algorithm described herein.

Geographical distance-based matching may identify a first and second address from different data sources and determine the distance between the addresses. In some embodiments, the addresses are converted to latitude/longitude (e.g., San Francisco, Calif. includes the latitude/longitude of 37.7833° N, 122.4167° W, etc.). These locations may be compared to determine the differences between the two addresses.

The conversion to latitude/longitude may also help identify differences between the addresses in a visual space (e.g., 2-dimensional plane). For example, the first and second addresses may be mapped and quickly identified as being very close or very far from other addresses that are previously associated with an existing object record. Based on this information, the system can determine whether or not to include any new addresses with an existing object record, based in part on the geographical distance-based matching.

When determining the field distance using geographical distance-based matching, various methods may be used. For example, the portions of the address may be compared, which may be similar to address matching (e.g., street number is compared with street number, etc.). In another example, the distances are compared to a pre-determined scale (e.g., 0-1 miles difference between the two addresses is a field distance of 10, 1-2 miles difference between the two addresses is a field distance of 20, etc.).

Phone number and location matching may compare one or more phone numbers from one data source (e.g., work, personal, etc.) with one or more phone numbers from a second data source, and may incorporate the address matching or geographical distance-based matching described above. The phone number portion of the matching may compare the phone numbers, digit by digit, as illustrated with the unique identifier-based matching. The difference between each data field may be used to determine the overall field distance (e.g., by aggregating the distances, a weighted combination or weighted average, etc.). In some embodiments, portions of the phone number may be compared and other portions may be skipped or disregarded (e.g., disregard an area code, disregard "1" or a country code, etc.).

In some embodiments, a standardization processes may be implemented with a matching algorithm (e.g., concurrently, near-simultaneously, etc.). For example, the process may identify a data field, like name, and create a normalized text string from the original data source. This may include changing capital letters to lowercase letters (and vice versa), removing characters or spaces, etc. The same may be done for other data attributes/fields from other data samples being matched. The two standardized text strings may be compared for similarities, which can create a uniform and comparable baseline for matching.

Phonetic matching may compare two data fields by indexing words by pronunciation. For example, a name data field from data source A may be phonetically compared with a name data field from data source B. The phonetic comparison may implement a variety of algorithms known in the art, including Soundex® (e.g., producing four-character strings composed of a single letter followed by three numbers, etc.), Metaphone®, or New York State Identification and Intelligence System (NYSIIS).

Each algorithm may analyze the data samples from a plurality of data sources, so that unique identifier-based matching produces one or more clusters, address matching produced one or more clusters, Geographical distance-based matching one or more clusters, etc. When each algorithm is implemented based on different rule sets, the resulting data clusters may be different for each algorithm. For example, a first algorithm may target field 1 (e.g., using unique identifier-based matching associated with the caregiver's NPI number) in the data sets and a second algorithm may target fields 2 and 3 (e.g., using phone number and location matching) in the data sets.

In some embodiments, the algorithms may be weighted. For example, a closer field distance (e.g., higher similarity, etc.) between two fields in unique identifier-based matching may be weighted higher than a closer field distance between two fields in geographical distance-based matching. In another example, the field distance for a particular field (e.g., the identifier) may be associated with the field distance for one or more fields in the cluster as well.

In some embodiments, one or more of the algorithms may be skipped. For example, each of the algorithms may be run except for fingerprinting (e.g., due to cost, delay, etc.). In another example, when the resulting clusters correspond with a distance below a threshold (e.g., distance of zero is a perfect match), other algorithms may be skipped based in part on the threshold or distance of a different algorithm.

The implemented algorithms and/or rule sets may result in proposed clusters, which may become new object records. Batch processing may be performed to create many new object records from a large amount of structured data with relative speed.

E. Two-Stage Clustering

In some embodiments, the clustering may be implemented in two steps. For example, the two steps may include partial clustering and optimized clustering. The partial clustering may involve a plurality of different sets of clusters that are clustered by different fields (e.g., clusters based on address, clusters based on name/address, clusters based on identifier, etc.). The optimized clustering may involve combining the different sets of clusters.

For example, as illustrated in FIG. 5, the algorithms 520 may form one or more partial clusters 530A, 530B, 530C, 530D, and 530E (hereinafter "clusters 530"). As illustrated, algorithm 520A determines one set of clusters 530A and 530B using the sample data 510, and algorithm 520B determines another set of clusters 530C, 530D and 530E using the same sample data 510. Algorithm 520A identified one or more similarities in the sample data in order to combine sample data 510A and 510B, but algorithm 520B did not identify the same similarities, causing three clusters to form instead of a combined two clusters.

The clusters may be combined and/or finalized 540. A final cluster is also called an optimum cluster. In some embodiments, the clustering engine 232 implements a clustering combination step after the clustering algorithm(s) have created one or more clusters.

Once the algorithm(s) have generated the clusters, the clustering engine 232 can create one optimum cluster set for one or more entities. As illustrated, the similar sample data 510A and 510B, which was used to form clusters 530A (by algorithm 520A) and clusters 530C, 530D (by algorithm 520B) can be combined into a single optimum cluster 550A. Sample data 510C, which was identified by both algorithms 520A and 520B as not similar to another data source to create clusters 530B and 530E, may be used to form a different optimum cluster 550B. Optimum cluster 550A may represent one entity and cluster 550B may represent one entity. If clusters 530 do not represent same entity, they may be imported and/or used to generate the optimum cluster as is.

1. Partial Clustering

Partial clustering of sample data may be implemented to create intermediate sets of clusters that might later form new object records of a database. New object records may be created for different types of objects, for instance providers, doctors, hospitals, practices, clinics, etc. For example, a text string may include one more characters that are parsed into a first name and a last name from a data source based on one or more rules (e.g., the location of the characters in a flat file from the data source, the location of a letter relative to other letters in the sample data, a location of a character after a certain number of comma separators in a *.CSV file from the data source, etc.).

The identification of the first name, last name, and other fields from the structured data may be based on one or more rules in order to become a cluster. In some embodiments, one or more of the rules may identify how closely the data can match the field in order to be clustered.

The rules may also identify data matches based on approximation. The text string may match a first name from second data when only one letter is different between the data sources (e.g., "John" vs. "Jon," etc.). In another example, the addresses may be slightly different between the two data sources and the structured data from each data source may still correspond with each other (e.g., "101 Main Street" vs. "101 E. Main St.," etc.).

The rules may also identify when structured data may be added to an existing cluster. For example, a cluster may include two rows of structured data that are determined to correspond with each other (e.g., matching names, matching addresses, fields that are similar within a threshold of each other to substantially match, etc.). New structured data may be received. The system 330 can determine whether the new structured data should correspond with the cluster. In some embodiments, given the new record, the clustering may identify the previously clustered records are within one cluster and then form a substantially new-version of the cluster.

The determination may include determining a field distance between one or more data fields. For example, a field distance may include a calculated representation of the difference between two data samples. The field distance may be calculated through fuzzy logic (e.g., a calculated score defining the similarity between two terms, etc.) or other similarity algorithm. Some algorithms may include string matching, fuzzy feature contrast (FCC), local sequence comparison, determining or incorporating a Minkowski distance, Euclidean distance, Manhattan distance, or any other algorithm known in the art for determining a distance on numeric or text string data. As with the previous illustration of "John" vs. "Jon," the field distance between a first field of the first sample in the cluster (e.g., the name of the existing structured data in the cluster) and the first field of the second sample (e.g., the name of the new structured data in the cluster) may be 0.4 because the differences between the two names is a single letter. However, a first field in a third sample of a cluster may include "Johnny" which may be associated with a field distance of 0.9 when compared with "Jon," even though "John," "Jon," and "Johnny" may correspond with the same or different people.

The method may include calculating a first metric based on the first field distance (e.g., 95% similar). The metric(s) can be any unit of measurement to compare two fields, including the field distances, text string lengths, confidence, or priority associated with the data source, and others discussed throughout the disclosure. For example, the system 330 can compare the fields of at least a portion of the structured data in the first cluster to determine the name and the geographical indicator for the first entity.

In some examples, calculating the metric based on the field distance includes calculating a weighted average of one or more field distances (e.g., a first field distance and one or more other field distances). The weighted average for the metric may be calculated when weights of at least two field distances are different.

When the new structured data is similar enough to the cluster, the new structured data may be added to the cluster (e.g., when the metric is within a threshold, including more than 75% matching, less than 10% different, etc.). In some examples, the cluster may be stored as a record in database 620. In some examples, a field may be updated in an existing cluster (e.g., update the middle name for a caregiver in an existing cluster, or store the name and the geographical indicator, etc.).

2. Optimized Clustering

Optimized clustering may be implemented in addition to partial clustering. For example, optimized clustering may identify similar clusters formed during partial clustering (e.g., through unique identifier-based matching, geographical distance-based matching, etc.). The similar clusters can form final partial clusters (sometimes referred to as "optimum clusters" or "optimized clusters").

A cluster distance may be calculated as part of optimized clustering. For example, the cluster distance may be an aggregated calculation of one or more of the fields in the cluster when compared with one or more of the fields in a different cluster (e.g., the similarities between the first name in each cluster, the similarity between the title in each cluster, etc.). The different sets of clusters may be combined with other clusters when the cluster distance between a first field in the first cluster and a first field in at least one the different sets of clusters is below a threshold (e.g., 0.5, greater than 0, less than 7, etc.).

The cluster distance may be calculated using various methods. For example, one or more data sets with corresponding data fields in the cluster may be pre-processed. The pre-processing may aggregate or combine the data fields of the one or more data sets in the cluster to identify similar data fields in the cluster. Those aggregated or combined data fields may be compared with other aggregated or combined data fields from other clusters to determine the distance (e.g., through majority voting discussed in Section IV, weighted average of one or more field distances, etc.). This process may create an intermediate data record, with corresponding intermediate field values that are used to determine the cluster distance between intermediate field values of another intermediate cluster. In other example, one or more random (predetermined) data sets with corresponding data fields in the cluster may be compared with another random data set in another cluster. In other example, an average of one or more data sets in a cluster may be compared to determine the cluster distance (e.g., ten data sets from one cluster are compared with five data sets from other cluster and the distances are averaged, etc.).

The similar clusters may be identified using one or more rules. For example, similar clusters may be identified based on one or more common fields (e.g., shared unique identifiers, shared phone number and name, shared address and phone number, etc.). In another example, similar clusters are based on relatively small field distances (e.g., a measurement of similarities or differences between two data fields in two clusters as defined by one or more clustering algorithms, etc.). The relatively small field distances may be determined based in part on a comparison of the field distance(s) with one or more thresholds. For example, when identifying a field distance (e.g., 10 out of 100, or 0.7 out of 1.0, etc.), the field distance may be compared with a threshold (e.g., 50, 0.5, respectively). The field distances below the cluster threshold(s) may be combined to help form the final partial clusters.

As an example illustration, Rule Set 1 and Rule Set 2 declare that a portion of sample data should belong to cluster A. Rule Set 3 declares that the same portion of the sample data should belong to cluster B. The sample data could then become part of cluster A or B, or both, depending on what rules are used to build the clusters. In some embodiments, the conflict in rules may be identified by a flag or transmitted as a notification for additional review. In some embodiments, a confidence value associated with the data source or data field can help determine whether the sample data should become part of cluster A or B, or both.

The quality of a sample data may be determined based in part on a confidence value. The confidence value may represent the field distance produced by applying one or more rules when determining how likely a sample belongs to a cluster. The confidence value may be stored with the cluster (e.g., in the master database 260). In some embodiments, the confidence value can correspond with the optimized cluster to describe the iterations and/or combinations of the cluster through the various rule sets. The confidence value may be normalized across different partial clusters to produce a comparable baseline.

The data source may be associated with a confidence value. For example, a certification data source may have a confidence value of 10 whereas a social networking website data source may have a confidence value of 1 or negative 5. In some embodiments, a data source is not used when the corresponding confidence value is below a confidence threshold (e.g., the data source is not used if the confidence value is below 0, etc.).

The confidence of a match can be used when creating optimum clusters. For example, if a rule set is known to provide a relatively significant number of false positive matches, the optimum cluster can leave these low confidence samples out to optimize further processing. The confidence can also be used in aggregation.

IV. Aggregation

Embodiments of the disclosure may determine aggregated data for one or more entities, performed by the aggregation engine 234. For example, once clusters have been generated from the raw and structured data, aggregation of the data may form a data object of an entity (e.g., caregiver data object, a facility data object, etc.). The data object of an entity may identify the most accurate data from the plurality of data sources for the particular entity.

Figure 7:
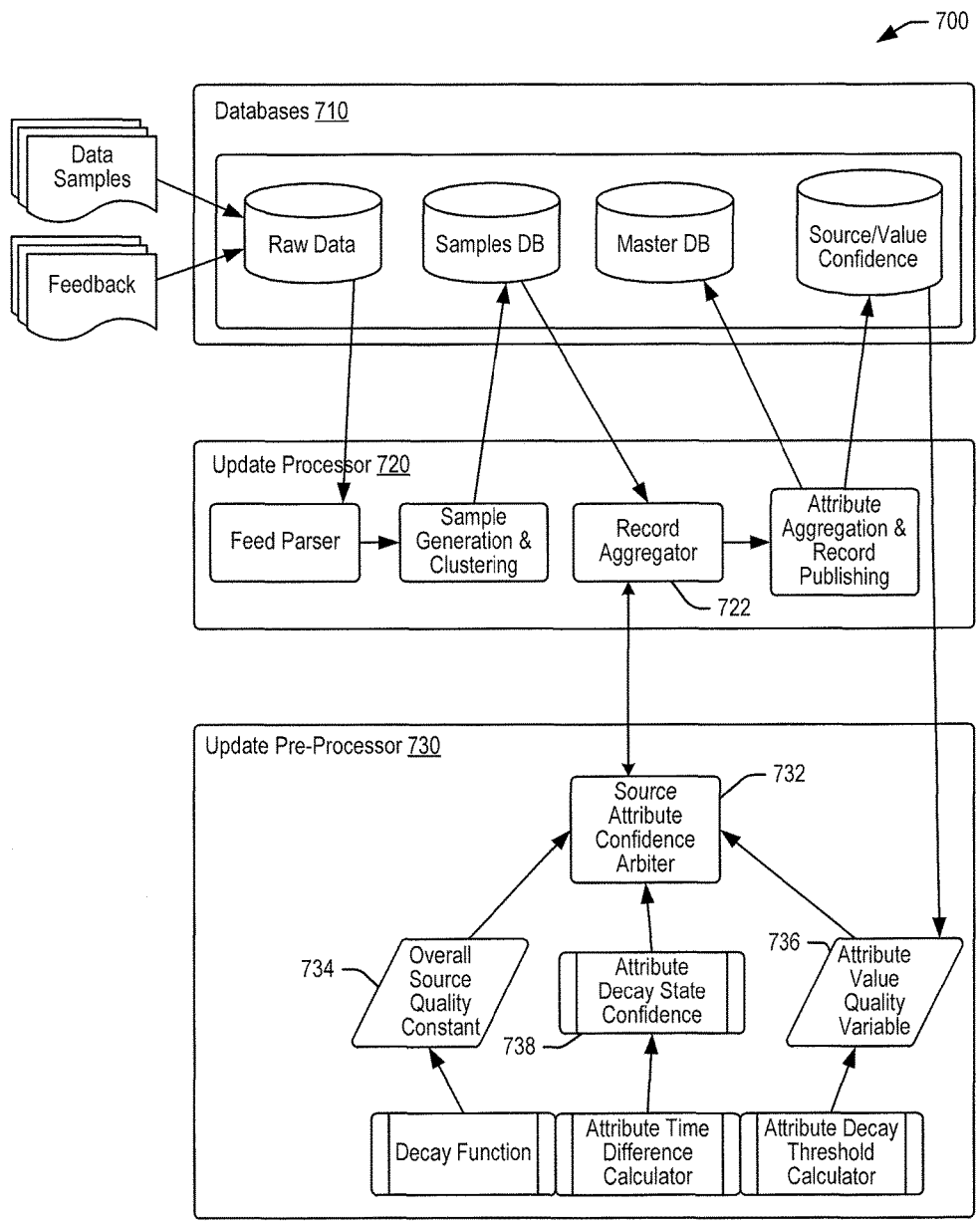
FIG. 7 shows an illustrative system for clustering and aggregating data according to an embodiment of the present invention.

FIG. 7 shows an illustrative system for clustering and aggregating data according to an embodiment of the present invention. In illustration 700, the system may include one or more databases 710 including a master database 260, application database 262, or other relevant databases or data tables (as identified throughout the disclosure, including in Sections II and VIII), an update processor 720 to implement clustering and aggregation (as identified throughout the disclosure, including Sections III and IV, which includes aggregation 722), and an update pre-processor 730 to implement decay analysis and attribution (as identified throughout the disclosure, including Sections V and VI). In aggregation 722, the data may be aggregated to form a data object of an entity. Additional details regarding FIG. 7 are provided in Section VI.

A. Aggregating a Cluster

One or more of the clusters may be aggregated. For example, the system may implement different algorithms with the optimum clusters to create or update object records based on the samples in each optimum cluster. In some examples, the clusters may be aggregated in a two-step process (e.g., partial then optimized clustering, etc.). After the aggregation process, the system may have formed one or more representations of object records, based in part on available sample data in the optimum clusters.

In a sample illustration, aggregation 722 can access each data sample in an optimum cluster. Aggregation 722 may generate an object record using one or more data fields from the optimum cluster for a single entity. For a particular object record, a single field (e.g., last name, address, etc.) may be accessed to identify the options for the correct data for that particular field. The value from one or more data sources may be chosen for the optimum cluster. For example, the data from the most reliable data source may be identified as the accurate data for the data object. In another example, the most frequent data from a plurality of data sources may be identified as the accurate data (e.g., five data sources claim the middle initial is "R.," but only one claims the middle initial is "E.," so the data record may choose "R.").

Various aggregation methods may be used. For example, data may be aggregated using best match selection, majority voting, or source prioritization. Each field in the final object record can be determined a different aggregation method (or the same aggregation method for each field) due to the unique properties of the field.

Best match selection can comprise counting the most frequent text string (e.g., including numbers, characters, symbols, etc.) in the optimized clusters and identifying that text string as the best match for the data field. Text strings associated with the data field that is not part of the common text string may be disregarded as the best match. The best match selection may be repeated one or more times to identify the most frequently used text string. In some embodiments, the text string(s) in a data field are disambiguated into portions of a text string to identify the best match (e.g., "Dr. Smith focuses on optometry" and "Dr. Smith focused on optometry" can be portioned into "Dr. Smith optometry" as a new description).

Majority voting includes choosing the most frequently used text string for each data field. For example, the optimized cluster may include fifty data samples that are related to a single caregiver (as identified through clustering). Thirty of the data samples may identify the caregiver's address as "100 Main Street" and ten of the data samples may identify the caregiver's address as "100 E. Main Street, Suite A." The aggregation process may identify that "100 Main Street" is correct for the single caregiver because the address is the most frequently used, and this address may be used as the correct address under a majority voting aggregation algorithm.

Source prioritization might consider the source of the data when determining which data to use in the aggregated data record. For example, data from a certification data source or the caregiver as a data source may be prioritized higher than a third party data source or social networking website. In some embodiments, aggregation 722 may systematically analyze which data samples are used, prioritized, valid, and ranked by source confidence to prioritize the most trusted sources. Historical data and/or data received from the caregiver may be associated with the highest priority. In another example, when a cluster has been changed (e.g., by a caregiver, by a data source, etc.), the other related clusters may be discarded and/or archived.

The clusters may be used for different purposes. For example, practice clusters associated with a medical facility and practice partial clusters may be aggregated for a medical facility and/or practice information. Information associated with these practice clusters may be used to identify which caregivers are associated with each practice cluster.

B. Aggregation Sub-Routines and Engines for Medical Practices

The aggregation may be implemented through one or more sub-routines or engines. These sub-routines or engines may determine the aggregated data based on one or more data objects, fields, data sources, or other information. For example, a base aggregator may identify a cluster and/or data sample for grouping. The base aggregator may report potential internal data conflicts and record possible data edit audits to the aggregation. In some embodiments, the base aggregator may initiate the rest of the aggregation and delegate the processing to different sub aggregators.

A profile aggregator may be implemented. For example, the profile and/or account information associated with a caregiver or practice may be obtained, with any symbols or spaces removed from the text string and/or capitalized letters changed (e.g., "John R. Doe" becomes "johnrdoe"). The selection of particular value for each field/attribute may be calculated by a weighted maximum likelihood algorithm for each field given the data source. A validness algorithm may also be considered.

A phone number, office hour, or insurance aggregator may be implemented. For example, the phone aggregator may identify a string of numbers in a cluster and/or data sample and remove one or more symbols from the numbers (e.g., "555-1212" becomes "5551212," etc.). The phone type and phone number may be identified as one text string instead of separate text strings. The phone aggregator may also provide the best possible landline and fax numbers for a caregiver and/or practice.

An address aggregator may be implemented. For example, the address aggregator may identify a string of numbers in a cluster and/or data sample and remove one or more symbols from the numbers (e.g., "101 Main Street"

becomes "101mainstreet," etc.). The address may be standardized (e.g., "St." becomes "street," an address identified by the United States Postal Service (USPS), etc.). In some embodiments, the address aggregator may attempt to determine the best locality information for addresses and geo-location for the address. The locality search may be a greedy algorithm, where the local maximum is maximized given an address in the locality collections. The geo-location may be pre-cached from external geocoding services, and assigned an address accordingly.

A status aggregator may be implemented. For example, the status aggregator may identify the status of the practice, active or not. In some embodiments, the status aggregator may determine whether the practice and/or caregiver is associated with malpractice or sanction cases related to this particular entity and update the status accordingly (e.g. no license due to malpractice claims=not an active practice).

In some embodiments, by using linked caregiver data samples and/or clusters in association with the practice cluster, the caregivers are being associated with an aggregated practice. A unique identifier associated with the practice may also be associated with the caregiver, causing some or all of the data associated with the practice to be associated with the caregiver. In some embodiments, the association requests are sent via the messenger to the message queue of the aggregation system.

A metadata aggregator may be implemented. For example, the metadata aggregator may compose the authors and history of the aggregation. In some embodiments, for each aggregation, an author may be associated with each data object. The aggregation counts and other metadata information such as aggregation time and internal data conflicts may also be determined and/or stored.

The updated practice information may be saved as a data object collection. This saved information may be stored with the application database 262 and accessed by a consumer application via an update signal to display to the care seeker, caregiver, or other users.

C. Aggregation Sub-Routines and Engines for Caregivers

After the practice aggregation, one or more aggregation sub-routines and engines may be implemented to determine aggregations of caregivers as well. In caregiver aggregation, the goal may be to extract the best possible caregiver information given the pre-processed, ordered, and/or filtered data samples in the clusters. Several sub-routines may be reused or repurposed for this method, including the base aggregator, profile aggregator, insurance aggregator, metadata aggregator, and status aggregator.

A specialty aggregator may be implemented. For example, the specialty aggregator may identify one or more possible specialties for the caregiver (e.g., based on frequency in the clusters, based on confidence values, based on title, etc.). Selection and validation of the data sources and fields may be considered as well to determine proper prioritization.

An education aggregator may be implemented. For example, the education aggregator may aggregate the education information, including medical school information, medical training information, internship, fellowships, and other information. The data associated with education may be treated as a complete entry. For example, graduation year, degree type, and institution information may be grouped together for more structured information gathering. Selection and validation of the data sources and fields may be considered as well to determine proper prioritization.

A publication aggregator may be implemented. For example, the publication aggregator may identify one or more publications by the caregiver. The caregiver may write and publish a series of articles about a topic that can be identified with the caregiver's profile and/or data object. Multiple articles may be aggregated as a group of publications.

A license aggregator may be implemented. For example, the license aggregator may identify the caregiver's license information. The latest and most valid license for the doctors may be extracted from the aggregation of multiple data sources. The license data may be compared with other data as well, including validating that the caregiver is associated with an active practicing record. Selection and validation of the data sources and fields may be considered as well to determine proper prioritization.

Internal information may be aggregated as well. For example, an identifier aggregator may be implemented. For example, the identifier aggregator may help identify the validity of a data sample for a caregiver (e.g., a license number, a drug enforcement administration (DEA) number associated with a prescribing active physician, etc.). The identifier may be used internally with the system to determine an active practicing record. In another example, a quality aggregator may be implemented (e.g., to help determine the final rating for the caregiver data object).

A rating aggregator may be implemented. For example, the rating aggregator may aggregate the publicly available rating information about a caregiver. The aggregated rating information can be used to calculate an overall rating score for the caregiver.

A caregiver practice association aggregator may be implemented. For example, the caregiver practice association aggregator may analyze dynamic changes to the practice. Different actions may be implemented based in part on the change performed. For example, when one caregiver is added a practice, the aggregator may associate the practice with the new caregiver data record. When a caregiver keeps an association with a practice, no action may be performed. When a caregiver is removed from the practice, the practice's information may no longer be associated with the caregiver, so that both caregiver and practice aggregated information may be updated.

D. Aggregation Prioritization and Confidence

Data sources may correspond with one or more confidence values, priorities, weights, or rankings. For example, one type of priority may help determine the relative trustworthiness of a data source. The American Medical Association (AMA) may be associated with a highest priority or confidence value for a particular data field (e.g., "10" confidence value, etc.), because this data source is the author of licensing information and is the original source of the data.

Data may be identified for the data record (e.g., in the optimum cluster) based in part on the confidence values (e.g., at a data source level, at a data field level, etc.). For example, when data is received from the AMA relating to licensing of the caregiver, the field(s) associated with the data may be chosen at a higher priority than other sources. Data may be chosen in various ways. For example, the data associated with the highest confidence value may be chosen as the source of the data for the particular data field. In another example, data associated with a higher weight or voting in determining the correct value may be chosen as the source.

The data sources may be associated with a relative weight in determining the correct value for an optimum cluster. For example, when a weight of a first data source is a "5" and a weight of a second data source is a "1," the data associated with the first data source may affect the final determination of the optimum cluster more than the second data source associated with the lesser weight. The data fields provided by the more trustworthy data source may be associated with the higher weight, identified in the optimum cluster, and more likely to be used in the data record (e.g., weighted voting).

In some embodiments, the confidence value may be associated with one or more data fields instead of an entire data sample. For example, the licensing board data source may provide a unique identifier that is associated with a high confidence value (e.g., "10"), in part because the licensing board generates the identifiers. The licensing board may also provide a caregiver's last name with the identifier, which might have changed and not updated with the licensing board. This data field from the licensing board data source may be associated with a lower confidence value (e.g., "7"). Instead, a state record data source may be associated with the a higher confidence value for the caregiver's last name (e.g., "8") and the caregiver itself may be associated with the highest confidence value for their own last name (e.g., "10").

Dynamic confidence values may also be implemented. For example, if an object record is found to contain an inaccuracy, the data source of the inaccurate information can be identified and its associated confidence value may be downgraded (e.g., from a "6" to a "3," etc.). The inaccurate information may be based on feedback (e.g., from a caregiver, from a care seeker, from a more accurate data source, etc.). The updated priority may improve the results of future aggregation processes. These adjustments can occur in real time and/or when feedback is received, so that object records are continuously improved for accuracy.

Data may be filtered and/or removed. For example, data sources and/or data fields associated with high confidence can be treated with precedence over samples with low confidence. In some embodiments, a data source associated with low confidence can be filtered from consideration completely. In some embodiments, the data source associated with low confidence may be considered only if no other data sources provide data for a particular field.

In some embodiments, a data record may not be generated (e.g., based on confidence associated with the data in the optimum cluster, based on flags/inaccuracies in the data, based on one or more messages during post aggregation, etc.). For example, a cluster may include a plurality of data fields that are associated with confidence values below a threshold (e.g., a potential caregiver cluster with a plurality of data fields, including last name associated with confidence of "4," license information with confidence of "3," education with confidence of "4," and threshold is "6"). When the confidence values of the cluster do not meet or exceed the threshold, an optimum cluster for the caregiver may not be generated and/or removed from the final set of caregivers.

In some embodiments, the data record may not be generated if there is a higher confidence data record that voids the low confidence sample data. For example, when one data source is identified as a prioritized data source (e.g., data source is a licensing board, manually entered data source, etc.), the prioritization of authoritative data source may prevent data generation. This may include examples when the caregiver is no longer practicing or does not want to be identified in a data record, a facility is no longer operational, or other reasons why the caregiver and/or facility may not be displayed to the care seeker. The prioritized data source may be identified in the master database 260 by a strong confidence value, prioritization flag, or other identifier that can efficiently identify the exception in the data processing for the particular entity.

E. Combining Multiple and Correct Entries in the Optimum Cluster

A plurality of data for a particular data field may be accurate and the optimum cluster may include one or more entries from the plurality of data. For example, a particular caregiver may be located at more than one location (e.g., 101 Main Street and 200 Beta Way, etc.). Some of the data sources may identify the first location and some data sources may identify the second location. When the confidence of each data source and/or data field is somewhat similar or exceeds a threshold, both locations may be associated with the optimum cluster. In this example, the caregiver may work out of location "101 Main Street" on Monday-Tuesday-Wednesday, and work out of location "200 Beta Way" on Friday-Saturday. Both locations may be helpful to display for potential and current care seekers.

In some embodiments, the determination for combining the multiple data sources may be based in part on the specialty of the caregiver (or other data field). For example, some specialties are rarely located in more than one location, corresponding with a higher/lower confidence value that a second location is accurate.

F. Incorporating Post Processing

Post processing may be implemented. For example, post processing may analyze created or updated object records as the result of the aggregation process. These post processing actions may be implemented as asynchronous action to speed up the overall aggregation, allowing better scalability of the implemented system due to near real-time processing requirements of the data pipeline. The actions may include, but are not limited to, statistical calculations, object record storage processing, and time consuming computations of different metrics.

Figure 9:
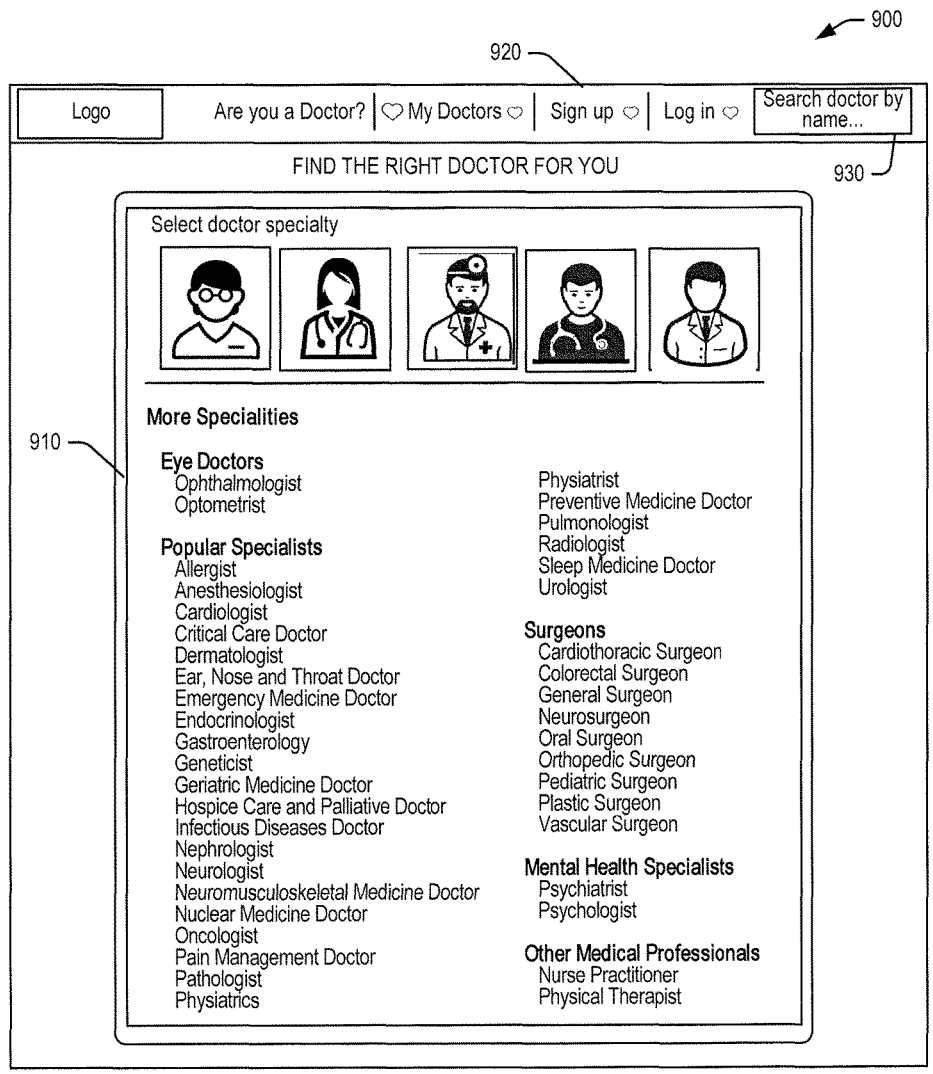
FIG. 9 shows a sample graphical user interface (GUI) according to an embodiment of the present invention.
Figure 10:
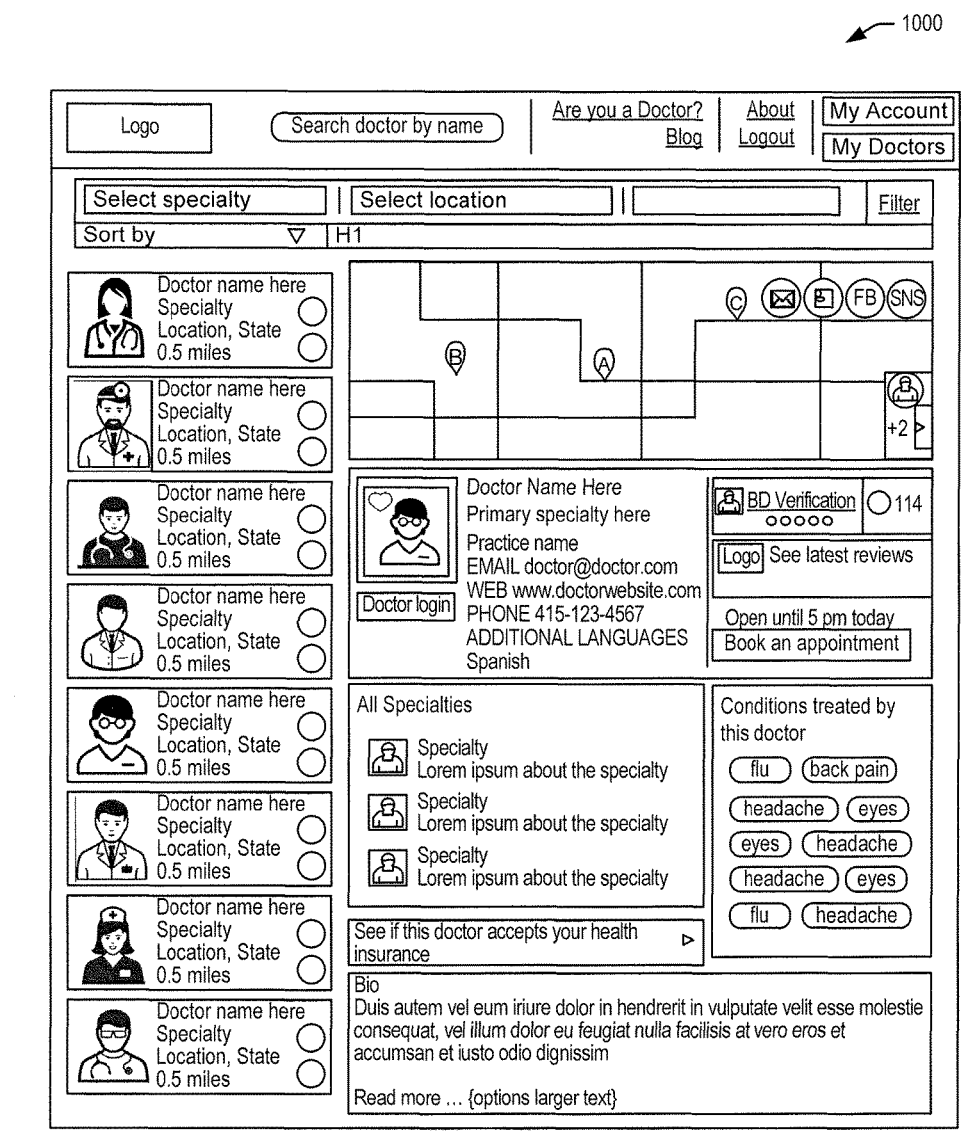

For example, the clustering and aggregation processes may identify a plurality of object records that are ready to display for a care seeker. Post processing may analyze the object records and prepare them for display, without publishing the object records to a user-facing interface or GUI. This intermediate step between clustering, aggregation, and display (as illustrated in FIGS. 9-10) can help the system 200, administrators, and/or caregivers validate the generated object records and their associations to ensure correct representation before publishing.

Post processing may identify incorrect information. For example, one or more data fields in an object record can be associated with a flag and/or low confidence value. The post processing can help alert a database administrator or proxy, or message a caregiver to request feedback about a questionable data sample.

Post processing may also identify new information (e.g., counts, associated information, summed data, etc.). As a sample illustration, a data sample may identify social network feedback associated with caregivers in a city that includes a relative ranking of the caregivers for that city (e.g., 1 out of 5 stars, ranking on a scale of 1 to 10, etc.). The data may be aggregated to create a summary or association as new data associated with the final data records (e.g., "This caregiver is ranked #5 out of all doctors in the city based on feedback!"). The method of identifying the new information may identify one or more records in a database that include the feedback from one or more users, compare the feedback (e.g., 4 stars is greater than 3 stars, so the caregiver associated with 4 stars should be better than the 3-star caregiver, etc.), generate a ranking associated with the combined feedback, and enable the ranking to be displayed on a graphical user interface (GUI), as illustrated in FIG. 10.

Post processing may also include one or more processes after one or more of the sub-aggregations have completed. One or more messages may be transmitted during aggregation to a message queue and analyzed. For example, with insurance data updates, the additional data may be requested from data sources through the messaging system (e.g., to confirm accuracy, to fix a pipeline error, etc.). When an error in processing arises, the data objects related to the errors may be deactivated, manually processed, and/or associated with a proper processing state. In some embodiments, an audit log may document the data validation, messaging, or alterations.

In another example, when a new caregiver is added to a practice, a reciprocal confirmation may be transmitted through a messaging service. The process may confirm that both data objects include similar information from the associating practice. When a caregiver remains with the practice, a validation message may be created and transmitted to ensure the reciprocal information is valid. When a caregiver is removed from a practice, a practice removal message may be transmitted to a proxy of the practice, the caregiver, or other entity to confirm the removal. In some embodiments, the change may be discarded when the practice did not perform the reciprocal operation. In some examples, the messaging system may contact a partner database or other data source to correct linked entities in these external systems.

Data may be flagged (e.g., for inaccuracies, based on feedback, changed from a score of "4" to a score of "1," etc.). When the data is used to generate the optimum cluster, a pipeline conflict may result. The pipeline conflict may identify one or more data sources or data fields that may be inaccurate. In some embodiments, the data may be filtered or removed if the data is inaccurate and replaced with other data that is not inaccurate. Future data samples received from the data source may also be identified in the master database 260 as being associated with previously inaccurate data.

V. Decay

Embodiments may alter data through decay analysis performed by the decay engine 236. For example, as caregivers move to different offices, receive additional certifications, and the like, the data received historically may become inaccurate. The system may associate the data with a decay rate. Over time, older data may become more inaccurate and less likely to affect the final data record, which helps to ensure that the data used in the data record is correct.

A. Decay Based on Data Source or Field

Figure 8:
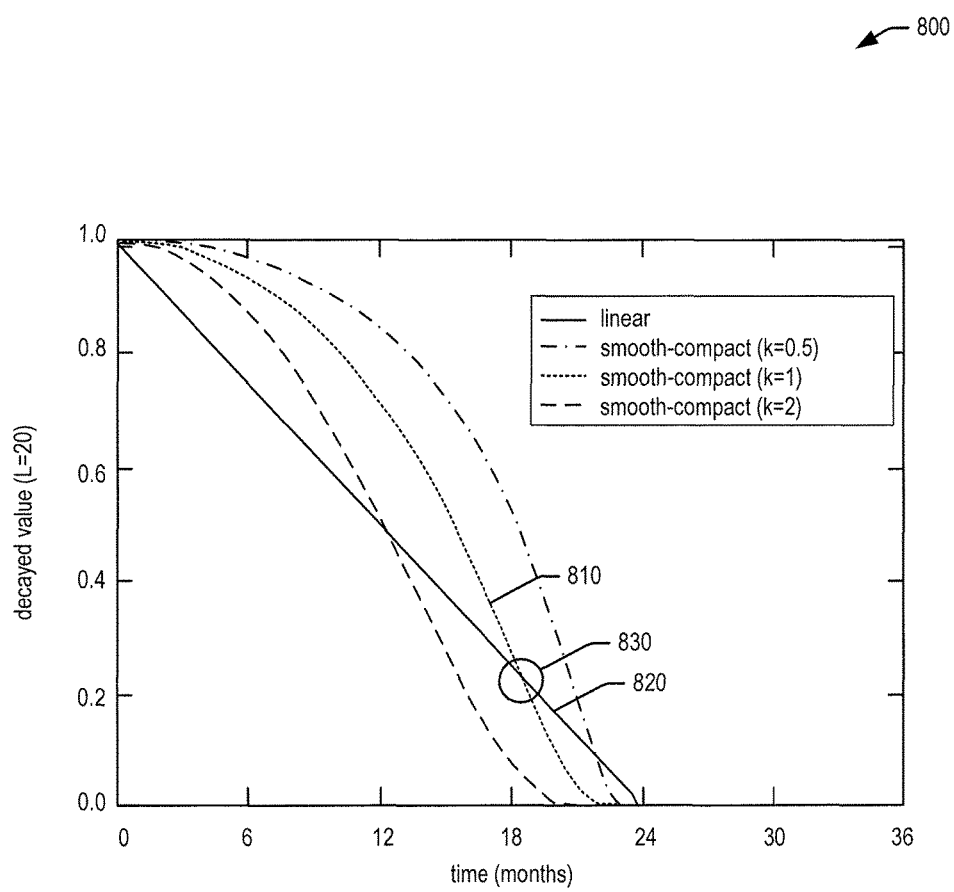
FIG. 8 shows an illustrative decay analysis according to an embodiment of the present invention.

FIG. 8 shows an illustrative decay analysis according to an embodiment of the present invention. In illustration 800, four data sources are displayed, including data source A 810 and data source B 820. The regression of the accuracy of the data may vary depending on a variety of factors, including data source (e.g., a data vendor, historical data stored in master database 260, the caregiver itself, etc.), field/data type (e.g., birthdate or license identifier of a caregiver may never change versus a caregiver's address may change more frequently, etc.), and time. For example, with a data source that is known for encouraging caregivers to keep their information up-to-date (e.g., a licensing board, etc.), the data may decay at a slower rate than a data aggregation data source.

The data associated with the highest value in relation to decay may be chosen as the more accurate data source and used in the aggregated data record. For example, data source A 810 and data source B 820 are both associated with a relatively high confidence at time zero, where decay has affected both sources the least. As time progresses, both data sources decay in value, becoming potentially less accurate. As illustrated, data source A 810 starts as a more accurate data source than data source B 820, and data source A 810 also decays at a faster rate than data source B 820. At time 830, the decay rate of data source A 810 causes data source A 810 to become potentially less accurate than data source B 820, so data source B 820 may be used in the aggregated data record after time 830. In some embodiments, data source B 820 may replace data source A 810 for one or more data fields for the entity in the aggregated data record in the database.

The decay of a data source and/or data field may be identified in the following description:

$$F(Q\,|\,T, A) = \frac{N_c}{N} \exp\left( |k - \delta_{N_c, A}| \left(1 - \frac{1}{1 - \left(\frac{t}{L}\right)^2}\right) \right)$$

The identified formula may be used to qualify the quality of the data source. For example, F is function, Q is quality, T is time, A is an attribute/field, $N_c$ is the count of a particular data source with attribute A, N is the count of a total data source with attribute A, k is the slope variable, $\delta_{N_c, A}$ is a predefined variable for attribute A with the data source, t is the current time when the decay value is calculated, and L is the maximum decay time constant. "Exp" refers to the exponent. The output of the function can identify how a particular data source decays over time as a function of the potential quality of the data sample, as illustrated in FIG. 8.

B. Attribute Quality Matrix

In some embodiments, an attribute quality matrix may be computed to determine the decay rate for one or more samples, data sources, and/or confidence values. The attribute quality matrix may consider a source authority, statistical determinations regarding the likelihood of accuracy for a data sample from the data source, source attribute/field quality, time since the data sample was received, and other information.

The decay may be reset. For example, a caregiver may access their profile or account with the system. The caregiver can access the data and/or provide a confirmation or feedback associated with data. Although new data has not been received, the decay on the data may be reset (e.g., decay of zero), so that the data identified in the caregiver's profile is determined to be relatively accurate and trusted more than one or more other data sources. In some embodiments, when the caregiver accesses only a portion of their profile, the portion of the profile may be associated with a reset decay value, but the non-accessed portions of the profile may be associated with a second decay value.

VI. Arbitration

Embodiments may alter data through arbitration performed by the arbitration engine 238. For example, the arbitration engine 238 may identify the historical choice of a particular field and/or data source used in the aggregated data record. In some embodiments, the field history can help identify the historical decision of the field value selection. This may help identify the data that was presented to a user at a certain time. This may also help prevent bad or invalid data from being incorporated with the aggregated data record (e.g., when data sources are consistently incorrect over time).

A. Method of Arbitrating Data

Data may be arbitrated. For example, system 200 may identify a data record (e.g., after clustering and aggregation, etc.) performed by the arbitration engine 238. The data record may be identified from a previous iteration of generating the data record that was stored in master database 260 and/or provided to a user via a GUI. The arbitration engine 238 may also identify the data source and samples used to create the data record in the master database 260. The master database 260 may also identify any change history associated with the data record (e.g., changing data field "title" from "DO" to "MD" or a new telephone number/addresses, etc.).

When new sample data is received from a data source, the arbitration engine 238 can identify the changed data in the new data source to determine if the change may be implemented to affect the data record. The data associated with the data record may be maintained (e.g., the change may not be implemented) when the change is similar to a previous change (e.g., the new data source includes "555-1212" and the data record was changed in January to "555-1111" from "555-1212"). In some embodiments, the confidence value and/or decay rate associated with the data source or data field may also be downgraded based on the inaccurate information as well.

In some embodiments, the confidence value associated with the data source for the new data may be compared to the confidence value associated with the data source and/or data field to determine which source is more trustworthy. When the confidence value of the old data source exceeds the confidence value of the new data source, the old data source may remain as the controlling data source in providing the data for the data record. Similarly, when the confidence value of a data field for the old data source exceeds the confidence value of the same data field for the new data source, the data field associated with the old data source may remain as the controlling data source for the data field (e.g., not the entire data record). No data fields may be replaced.

B. Arbitration Using Historical Data

With arbitration, a field may be associated with multiple attribute values that are invalidated with historical data. For example, a particular caregiver may be associated with MD, DO, PhD, and other titles from multiple sources of data, but the historical data may identify that the caregiver should only be associated with MD. The other title entries from incorrect data sources may be flagged as invalid together with the arbitration value history. The flag may be stored in a metadata structure. The determination of this signal can also have an impact on overall quality matrix explained above.

In some embodiments, the arbitration may be implemented by first identifying a value change in the database. This may consist of a pool of value changes on each attributes/fields and its origin identifier of the value. The data may correspond with one or more data fields, including an attribute/field, reason, origin, timestamp, etc. In some embodiments, the clustering algorithm used in the previous clustering process may be used to regenerate the data using the same clustering algorithm.

Second, the historical value may be identified. For example, when a new value change proposal is introduced, one embodiment of arbitration may look through the history by the searching for the related origin data source and related attributes/fields. If the historical value has been flagged as inaccurate, the future value may also be flagged. The method may avoid assigning invalidated values and choose the value that is selected before.

Next, the value may be selected based in part on feedback. For example, the value changes may be provided to the caregiver (e.g., in the profile or account, through a messaging system, etc.). The method may receive feedback from the caregiver to determine the correctness of the value. The feedback may be used to incorporate the more accurate value to the database (e.g., master database 260) and/or used to update the decay function (described in Section V).

C. Illustrative System Components for Arbitration

Returning to FIG. 7, the arbitration engine 732 is illustrated with the update pre-processor 730. An example of the arbitration engine is also illustrated in FIG. 2 at arbitration engine 238.

As illustrated in FIG. 7, the arbitration engine 732 is a component that helps decide what value a particular attribute gets when there are multiple choices and value histories. The arbitration engine 732 determines when to evaluate the possible outcome. The arbitration engine 732 may utilize several sub components to calculate one or more possible values for given attributes/fields. The sub components may include an overall source quality constant 734, attribute value quality variable 736, or attribute decay state confidence 738.

The overall source quality constant 734 may be used to help identify a general confidence value associated with a data source. The overall source quality constant may be calculated from the overall quality attribute authority and confidence matrix or attribute quality matrix. In some embodiments, the overall source quality constant may incorporate a confidence value for the data source over time, so that when a data source is consistently accurate (e.g., the sample data from the data source may be used in the data record, the sample data may match a large number of data sources to be considered more accurate in the aggregate, etc.), the data may be more trustworthy over time.

The attribute value quality variable 736 may also be used to help determine arbitration for a data sample. The attribute value quality variable may access the possible value histories for a particular attribute/field or data source. The attribute value quality variable 736 may be used to calculate which values the arbitration engine should not use during the history decisions.

In some embodiments, the overall source quality constant 734 and the attribute value quality variable 736 may be used in combination to identify a confidence value for a data field. For example, the overall source quality constant 734 may identify the data source as a historically trustworthy data source and the attribute value quality variable 736 may identify the data field as a historically trustworthy data field. In some embodiments, the constants can be weighted (e.g., the overall source quality constant 734 is 60% of the total confidence value and the attribute value quality variable 736 is 40% of the total confidence value, etc.). The combined confidence value may help identify the accuracy of the data over time.

In some embodiments, the overall source quality constant 734 or the attribute value quality variable 736 may be lowered or weighted. The alteration of the constant(s) may help determine which data source and/or data field would be chosen in a weighted voting scenario and/or to help with choosing which data field or data source to use in the instance of a tie.

The attribute decay state confidence 738 may also be used to help determine arbitration for a data sample. The attribute decay state confidence may help to calculate the value history for an attribute/field using a decay function, attribute time difference calculator, and attribute decay threshold calculator. The decay function may include an inverse exponential function with respect to the length of time the value is assigned to the attribute. The attribute time difference calculator can determine the length of time the value has been assigned to the attribute. The attribute decay threshold calculator may correspond with a constant and/or determine the length of time associated with trusting the accuracy of a given attribute/field value change.

The arbitration engine 732 may also act recursively. For example, after each aggregation, the aggregated results and the difference between the assignment of the value and the history may be used as input in future iterations and stored with the arbitration history to use as a learning signal for the system.

D. Version Control

The data associated with the optimum cluster, displayed data (in a profile, in a graphical user interface (GUI) for a care seeker, etc.) may be stored for version control. This information can be used to identify one or more of the decision flows and potentially correct previously made incorrect assumptions.

In some embodiments, the history of the optimum cluster formation may be stored at various points of time. The history information may be stored for each clustering, in order to be able to understand the dynamic of the sample clusters and aggregation. The history information may be stored for each run of the optimum clusters (e.g., with version identification, including version 1.1, version 1.2, etc.). The history information may be stored during implementation as well.

VII. Reporting Data

Embodiments of the disclosure may generate and provide analytics performed by the reporting engine 240. For example, once an optimum cluster is identified for caregiver A and caregiver B, information associated with these caregivers may be provided to users through a graphical user interface.

A. Displaying Data in a GUI

FIG. 9 shows a sample graphical user interface (GUI) according to an embodiment of the present invention. In illustration 900, the care seeker (e.g., a user operating a user device to access the webpage, etc.) may select a particular specialty 910 associated with one or more caregivers. The specialties may be accessed by links corresponding to one or more caregivers, including eye doctors (e.g., ophthalmologists, optometrists, etc.), surgeons, and other specialties (e.g., allergists, anesthesiologists, nurse practitioner, physical therapist, etc.). In some embodiments, the care seeker may also sign up or access a profile or account through a tool 920 on the webpage.

In some embodiments, the care seeker may search for a caregiver using a search tool 930. The GUI may be configured to receive one or more queries from the care seekers (e.g., query includes "eye doctor in San Francisco, Calif.", etc.). The system may obtain caregivers relevant to the query and provide the relevant caregivers and/or practices in response to receive the query. The caregivers may be associated with a specified category of service.

FIG. 10 shows a sample graphical user interface (GUI) according to an embodiment of the present invention. In illustration 1000, relevant caregivers and/or practices are provided for the care seeker. The GUI may display information associated with the optimum cluster for the caregiver (e.g., the most accurate name, location, specialty, etc.) and other information that might be relevant for the care seeker. In some embodiments, other relevant caregivers may be displayed with the GUI as well.

In some embodiments, analytics based on data may be generated, provided, and displayed to care seekers. Analytics may also be useful to caregivers, in that the analytics can be used to produce business leads and convey insights to caregivers that otherwise might be difficult to realize. Analytics can be user-specific, such that they are tailored to the recipient based on the received data.

The data may be organized in ways that are useful to the users. For instance, the GUI may display to a care seeker the best potential caregivers (e.g., as determined by the system based on the care seeker's search query and other relevant data). The results may be ordered or ranked. Caregivers in this list of results who have openings in their calendar (e.g., during a particular time frame) might be highlighted to draw extra attention from the care seeker.

B. Providing a Customized GUI

A care seeker's interactions with the GUI may be tracked to generate analytics. For example, when 50% of the care seekers request additional information about a caregiver's education, the education data associated with the profile may be highlighted or reorganized for easier access.

In some embodiments, analytics can provide suggestions to users to improve the user experience. For instance, analytics may show that a certain doctor is receiving very few profile visits, and that the profile is missing key information. The GUI may display a message to the care giver (e.g., through the care giver's profile, etc.) associated with the missing information.

In some embodiments, the system may initiate an advertising campaign to bolster a care giver's online presence. The advertisement may be displayed through the GUI illustrated in illustration 1000. The analytics may be identified automatically in real-time, so that the care seekers can receive the assistance quickly and efficiently.

VIII. Storing Data Through a Separation of Application Database and Master Database Embodiments of the disclosure may store data, perform version control, and allow the system to access historical data performed by the historical data engine 242. For example, the system can comprise a master database 260 and an application database 262.

The master database 260 can store records of entities and that is communicably coupled with a plurality of application databases, the master database having a master data structure for accessing the records. In some embodiments, the master database 260 can be configured to store a temporary value of a data field to allow the system to determine whether to update the value in another data object of the master database 260. If the value is to be updated, the master database can be configured to use the value of the first field to determine a master value of the first field. The master database can be configured to send the master value to the application database.

The application database 262 can be configured to store a value of a first field of a first record of a first entity. The first application database can have a first data structure that is different than the master data structure. The application database 262 can be configured to send the value of the first field to a master database. The application database can be configured to store the master value of the first field for retrieval by users of the first application database.

The abstraction of the master and application databases described above may be beneficial for performance. Master databases are typically not structured in ways to enable certain actions to be completed quickly (for instance geographical queries). By allowing applications to define their own databases, they can be suited to meet the dynamically changing needs by various users and entities.

In one example, an application database may be devoted specifically to care seekers. This may be a highly specialized database that allows for fast queries based on the location of a caregiver and other parameters. There may be a separate application database devoted specifically to caregivers, which may be optimized on analyzing and maintaining relationships and ensuring that caregiver data is always correct. Data from the master database may be provided to these separate applications in different ways, depending on the needs of those applications.

The abstraction of the master database and application databases also allows for data changes to flow between them. For instance, a doctor may edit their corresponding profile information, which produces a change in the data in the application database. The change is mapped to the structure and format of master data so that the change can be implemented with the master database. After this occurs, clustering, aggregation, and other processes may occur in real time. When the object record in the master database is changed and validated, the change may be implemented to the desired application database(s). This change may or may not reflect exactly what was originally changed in the user-facing application, based on a variety of factors, including the original change originated with an untrusted source, was illogical, etc. The benefit of this process includes version control, and efficiently providing changes to the user-facing GUI (e.g., speeding up the processing time with the master database regarding clustering, aggregation, etc.).

IX. Computer System

Figure 11:
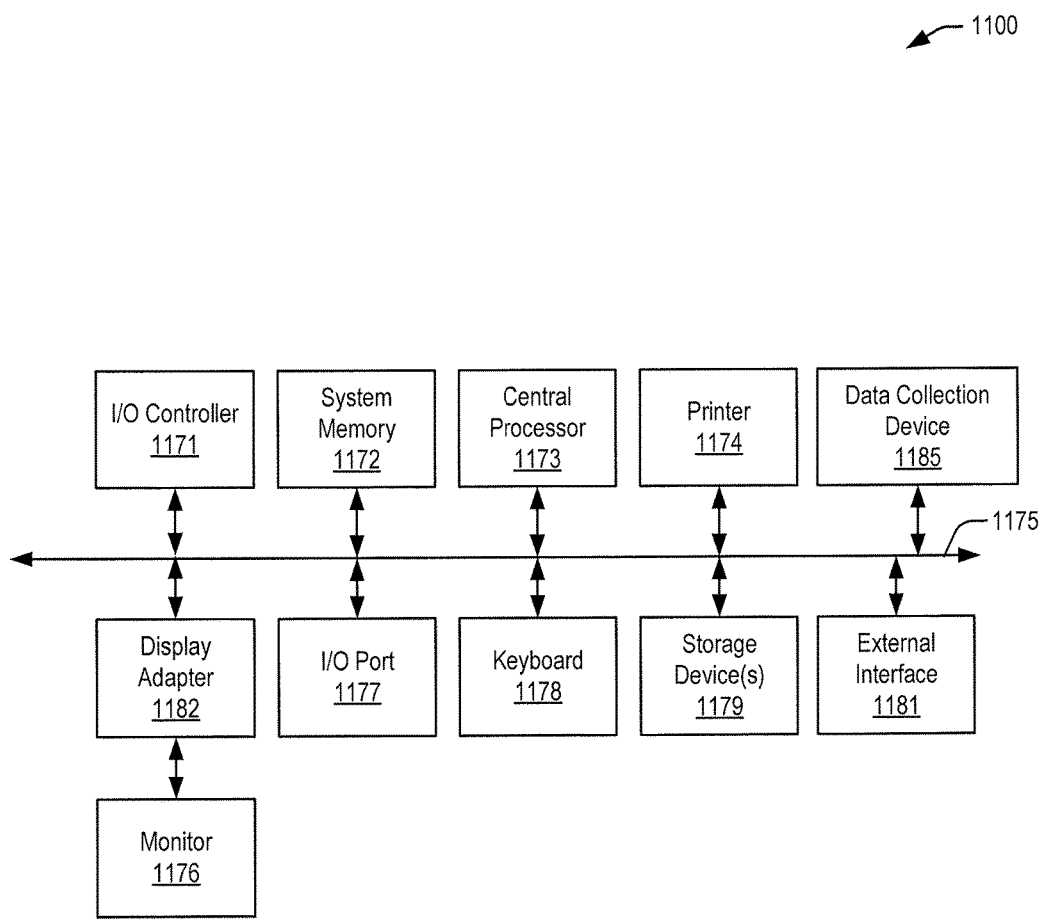
FIG. 11 shows a block diagram of an example computer system usable with systems and methods according to embodiments of the present invention.

Any of the computer systems mentioned herein may utilize any suitable number of subsystems. Examples of such subsystems are shown in FIG. 11 in computer apparatus 1100. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 11 are interconnected via a system bus 1175. Additional subsystems such as a printer 1174, keyboard 1178, storage device(s) 1179, monitor 1176, which is coupled to display adapter 1182, and others are shown. Peripherals and input/output (I/O) devices, which couple to I/O controller 1171, can be connected to the computer system by any number of means known in the art such as input/output (I/O) port 1177 (e.g., USB, FireWire®). For example, I/O port 1177 or external interface 1181 (e.g. Ethernet, Wi-Fi, etc.) can be used to connect computer system 1100 to a wide area network such as the Internet, a mouse input device, or a scanner. The interconnection via system bus 1175 allows the central processor 1173 to communicate with each subsystem and to control the execution of instructions from system memory 1172 or the storage device(s) 1179 (e.g., a fixed disk, such as a hard drive or optical disk), as well as the exchange of information between subsystems. The system memory 1172 and/or the storage device(s) 1179 may embody a computer readable medium. Another subsystem is a data collection device 1185, such as a camera, microphone, accelerometer, and the like. Any of the data mentioned herein can be output from one component to another component and can be output to the user.

A computer system can include a plurality of the same components or subsystems, e.g., connected together by external interface 1181 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, Lisp, Clojure, or scripting language such as Perl, Ruby, or Python using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary.

All patents, patent applications, publications, and descriptions mentioned herein are incorporated by reference in their entirety for all purposes. None is admitted to be prior art.

What is claimed is:

1. A method of aggregating entity data from a plurality of sources, the method comprising:
   obtaining sample data from a plurality of data sources, the sample data corresponding to a plurality of entities that have not been previously identified, wherein samples from multiple data sources correspond to a same entity;
   processing the samples to identify a plurality of fields corresponding to each sample;
   identifying a first partial cluster of the samples based on a first set of rules that relies on a geographical indicator, the first partial cluster comprising a first subset of fields from a first sample for comparison with a second sample on the first subset of fields to determine whether the samples correspond with a same entity, wherein identifying the first partial cluster includes:
   determining whether the second sample is in the first partial cluster by:
      determining a first field distance between a first field of the first subset of fields of the first sample and a first field of the first subset of fields of the second sample;
      calculating a first metric based on the first field distance; and
      adding the second sample to the first metric when the first metric is within a first threshold;
   identifying a second partial cluster of the samples based on a second set of rules that relies on a user identifier, the second partial cluster comprising a second subset of fields from the first sample for comparison with the second sample on the second subset of fields to determine whether the samples correspond with the same entity, wherein identifying the second partial cluster includes:
   determining whether the second sample is in the second partial cluster by:
      determining a second field distance between a second field of the second subset of fields of the first sample and a second field of the second subset of fields of the second sample;
      calculating a second metric based on the second field distance; and
      adding the second sample to the second metric when the second metric is within a second threshold;
   initiating an aggregation process that determines that the second partial cluster of the samples corresponds to the same entity as the first partial cluster of the samples, wherein the aggregation process generates a full entity cluster that corresponds to the same entity having the user identifier for the first field and the geographical indicator for the second field; and
   storing the user identifier and the geographical indicator of the full entity cluster into a first record of a database.

2. The method of claim 1, the method further comprising:
   identifying which data source the samples are from;
   determining confidence values corresponding to the data source; and
   using the confidence values to determine the user identifier and the geographical indicator.

3. The method of claim 2, wherein at least one field of a sample from the data source is not used when the confidence values for the data source are below a confidence threshold.

4. The method of claim 2, further comprising:
   receiving feedback from a first entity regarding the first record; and
   computing the confidence values based on the feedback.

5. The method of claim 1, wherein the first threshold, the first field, and the first metric are specified by the first set of rules.

6. The method of claim 1, wherein the first set of rules specifies multiple fields for clustering the samples, each of the specified fields having a corresponding field distance.

7. The method of claim 6, wherein calculating the first metric based on the first field distance includes:
   calculating a weighted average of the first field distance and one or more other field distances of the corresponding field distances, wherein weights of at least two field distances are different.

8. The method of claim 1, further comprising:
   for each of one or more additional sets of rules:
      identifying an additional cluster of the samples as corresponding to the first entity;
      comparing the samples of the first cluster and the one or more additional clusters to determine samples in a first optimum cluster; and
      determining the user identifier and the geographical indicator for the first entity by comparing the fields of samples in the first optimum cluster.

9. The method of claim 8, wherein at least two different sets of rules specify different fields to use for clustering the samples.

10. The method of claim 1, wherein the first field distance and the second field distance are determined using local sequence comparison that identifies similarities between corresponding fields in the first sample or the second sample corresponding with the first partial cluster or the second partial cluster.

11. The method of claim 1, further comprising:
   determining first representative fields of the first partial cluster by comparing the fields of the samples in the first partial cluster; and
   determining second representative fields of the second partial cluster by comparing the fields of the samples in the second partial cluster,
   wherein the one or more field distances are determined using one or more corresponding fields of the first representative fields and the second representative fields.

12. The method of claim 1, further comprising:
   determining that a first data source is associated with a higher confidence value than a second data source, the first data source and second data source included in the plurality of data sources;
   determining that the first data source is an origin of data for the first record in the database based in part on the higher confidence value;

calculating a first decay rate for a first confidence value for the first data source and a second decay rate of a second confidence value for the second data source;

determining that the first data source is less accurate after a time than the second data source based in part on the first confidence value being less than the second confidence value; and altering the first record in the database to correspond with the second data source in the database based on the first and second confidence values.

13. The method of claim 1, further comprising:

identifying the first record of the database to include first feedback;

comparing the first feedback associated with the first record of the database with second feedback associated with other records of the database;

generating a ranking of the records in the database based in part on the first feedback associated with the first record and the second feedback associated with the other records; and enabling the ranking to display on a graphical user interface.

14. The method of claim 1, further comprising:

identifying the first record of the database, wherein the first record includes the first field from a first data source in the plurality of data sources;

obtaining new sample data from a second data source in the plurality of data sources, wherein the new sample data includes a different value for the first field compared to the first record;

determining a new confidence value associated with the new sample data, wherein an existing confidence value is associated with the first data source or the first field corresponding with the first record of the database;

determining that the new confidence value associated with the new sample data is less than the existing confidence value associated with the data source or first field corresponding with the first record of the database; and maintaining the first record as unchanged despite the new sample data.

15. The method of claim 1, further comprising:

upon analyzing the full entity cluster, identifying a second entity cluster from the full entity cluster, wherein the second entity cluster corresponds with the full entity cluster by the geographical indicator for the full entity cluster; and duplicating and storing the geographical indicator for the full entity cluster as a new geographical indicator for the second entity cluster.

16. The method of claim 15, wherein a second entity name field of the second entity cluster corresponds to a third field of the full entity cluster.

17. The method of claim 1, wherein other fields of the first sample and the second sample are telephone numbers.

18. The method of claim 1, wherein the aggregation process to generate the full entity cluster is performed in a hierarchy optimum cluster comprising:

determining the first field comprises the user identifier as a first most frequent entry with a first highest quality score in the first partial cluster; and determining the second field comprises the geographical indicator as a second most frequent entry with a second highest quality score in the second partial cluster.

19. The method of claim 1, wherein the first partial cluster and second partial clusters are stored and reused in a different aggregation process to generate the full entity cluster.

20. The method of claim 1, wherein the aggregation process comprises:

determining a first frequency for each single entry of the geographical indicator from the first partial cluster;

generating a data object for the full entity cluster that includes the single entry of the geographical indicator when the first frequency for the single entry exceeds a third threshold;

determining a second frequency for each single entry of the user identifier or the name from the second partial cluster; and updating the data object for the full entity cluster that includes the single entry of the user identifier or the name when the second frequency for the single entry exceeds a fourth threshold.

21. The method of claim 20, wherein the aggregation process implements a phonetic algorithm.

22. A computer product comprising a non-transitory computer readable medium embodying thereon a set of instructions, which when executed by a computer system cause the computer system to perform the steps of:

obtaining sample data from a plurality of data sources, the sample data corresponding to a plurality of entities that have not been previously identified, wherein samples from multiple data sources correspond to a same entity;

processing the samples to identify a plurality of fields corresponding to each sample;

identifying a first partial cluster of the samples based on a first set of rules that relies on a geographical indicator, the first partial cluster comprising a first subset of fields from a first sample for comparison with a second sample on the first subset of fields to determine whether the samples correspond with a same entity, wherein identifying the first partial cluster includes:

determining whether the second sample is in the first partial cluster by:

determining a first field distance between a first field of the first subset of fields of the first sample and a first field of the first subset of fields of the second sample;

calculating a first metric based on the first field distance; and adding the second sample to the first metric when the first metric is within a first threshold;

identifying a second partial cluster of the samples based on a second set of rules that relies on a user identifier, the second partial cluster comprising a second subset of fields from the first sample for comparison with the second sample on the second subset of fields to determine whether the samples correspond with the same entity, wherein identifying the second partial cluster includes:

determining whether the second sample is in the second partial cluster by:

determining a second field distance between a second field of the second subset of fields of the first sample and a second field of the second subset of fields of the second sample;

calculating a second metric based on the second field distance; and adding the second sample to the second metric when the second metric is within a second threshold;

initiating an aggregation process that determines that the second partial cluster of the samples corresponds to the same entity as the first partial cluster of the samples, wherein the aggregation process generates a full entity cluster that corresponds to the same entity having a user identifier for the first field and the geographical indicator for the second field; and storing the user identifier and the geographical indicator of the full entity cluster into a first record of a database.

23. The computer product of claim 22, the steps further comprising:

identifying which data source a sample is from;

determining confidence values corresponding to the data source; and using the confidence values to determine the user identifier and the geographical indicator for the first entity.

24. The computer product of claim 22, wherein at least one field of a sample from the data source is not used when the confidence values for the data source are below a confidence threshold.

25. The computer product of claim 22, further comprising:

receiving feedback from the first entity regarding the first record; and computing the confidence values based on the feedback.

* * * * *